(12) United States Patent
Shan et al.

(10) Patent No.: US 6,465,258 B1
(45) Date of Patent: Oct. 15, 2002

(54) FXR RECEPTOR-MEDIATED MODULATION CHOLESTEROL METABOLISM

(75) Inventors: Bei Shan, Redwood City; Arthur Y Okamoto, San Mateo, both of CA (US)

(73) Assignee: Tularik, Inc., South San Francisco, CA (US)

( * ) Notice: Subject to any disclaimer, the term of this patent is extended or adjusted under 35 U.S.C. 154(b) by 0 days.

(21) Appl. No.: 09/478,948

(22) Filed: Jan. 6, 2000

Related U.S. Application Data
(60) Provisional application No. 60/115,249, filed on Jan. 7, 1999.

(51) Int. Cl.$^7$ ...................... G01N 33/566; G01N 33/53; C12Q 1/68; A61K 38/16
(52) U.S. Cl. ............................ 436/501; 435/6; 435/7.1; 530/358
(58) Field of Search ...................... 435/6, 7.1; 530/358; 436/501

(56) References Cited

U.S. PATENT DOCUMENTS

| | | | |
|---|---|---|---|
| 5,071,773 A | | 12/1991 | Evans et al. |
| 5,582,981 A | | 12/1996 | Toole et al. |
| 6,005,086 A | * | 12/1999 | Evans et al. |

OTHER PUBLICATIONS

Mangelsdorf et al., "The RXR Heterodimers and Orphan Receptors," Cell, 83:841–850 (1995).
Martinez et al., "The estrogen–responsive element as an inducible enhancer: DNA sequence requirements and conversion to a glucocorticoid–responsive element," EMBO Journal, 6(12):3719–3727 (1987).
McInerney et al., "Determinants of coactivator LXXLL motif specificity in nuclear receptor transcriptional activation," Genes & Dev., 12–3357–3368 (1998).
Miesfield et al., "Glucocorticoid Receptor Mutants That Define a Small Region Sufficient for Enhancer Activation," Science, 236:423–427 (1987).
Rhodes et al., "Zinc Fingers," Scientific American, pp. 56–65 (Feb. 1993).
Schindler et al., "Components of a Stat Recognition Code Evidence for Two Layers of Molecular Selectivity," Immunity, 2:689–697 (1995).
Seol et al., "Isolation of Proteins That Interact Specifically with the Retinoid X Receptor Two Novel Orphan Receptors," Mol. Endocrinol., 9:72–85 (1995).
Singhal et al., "Effect of Cholesterol and Bile Acids on the Regulation of Cholesterol Metabolism in Hamster," Biochim. et Biophysica Acta, 752:214–222 (1983).
Zavacki et al., "Activation of the orphan receptor RIP14 by retinoids," Proc. Natl. Acad. Sci. USA, 94:7909–7914 (1997).

Zhou et al., "Nuclear Receptors Have Distinct Affinities for Coactivators: Characterization by Fluorescence Resonance Energy Transfer," Mol. Endocrinol., 12(10):1594–1604 (1998).
Darimont et al., "Structure and specificity of nuclear receptor–coactivator interactions," Gens & Dev., 12:3343–3356 (1998).
Enmark et al., "Orphan Nuclear Receptors–The First Eight Years," Mol. Endocrinology, pp. 1293–1307 (1996).
Evans, "The Steroid and Thyroid Hormone Receptor Superfamily," Science, 240–889–895 ((1988).
Forman et al., "Identification of a Nuclear Receptor That is Activated by Farnesol Metabolites," cell, 81:687–693 (1995).
Giguére et al., "Functional Domains of the Human Glucocorticoid Receptor," Cell, 46:645–652 (1986).
Green et al., "A superfamily of potentially oncogenic hormone receptors," Nature, 324:615–617 (1986).
Green et al., "Oestradiol induction of a glucocorticoid–responsive gene by a chimaeric receptor," Nature, 325:75–78 (1987).
Hollenberg et al., "Colocalization of DNA–Binding and Transcriptional Activation Functions in the Human Glucocorticoid Receptor," Cell, 49:39–46 (1987).
Jantzen et al., "Cooperativity of Glucocorticoid Response Elements Located Far Upstream of the Tyrosine Aminotransferase Gene," Cell, 49:29–38 (1987).
Keegan et al., "Separation of DNA Binding from the Transcription–Activating Function of a Eukaryotic Regulatory Protein," Science, 14:699–704 (1986).
Laudet et al., "Evolution of the nuclear receptor gene superfamily," EMBO Journal, 11(3):1003–1013 (1992).
Lehmann et al., "An Antidiabetic Thiazolidinedione is a High Affinity Ligand for Peroxisome Proliferator–activated Receptor γ (PPARγ)," J. Biol. Chem., 270(22):12953–12956 (1995).
Makishima et al., "Identification of a Nuclear Receptor for Bile Acids," Science, 284:1362–1365 (1999).

(List continued on next page.)

*Primary Examiner*—Ethan C. Whisenant
(74) *Attorney, Agent, or Firm*—Townsend and Townsend and Crew LLP

(57) ABSTRACT

This invention provides methods and compositions that are useful for modulating cholesterol levels in a cell, and for identifying compounds that can tested for ability to modulate cholesterol levels in mammals. In vitro assays for prescreening to identify candidate therapeutic agents for modulation of cholesterol metabolism are provided. These methods involve analyzing the effect of a test compound on the binding of FXR to a ligand for FXR. Such ligands include, for example, bile acids, coactivators, and corepressors. The methods and compositions involve modulating FXR-mediated expression of genes involved in cholesterol metabolism.

47 Claims, 14 Drawing Sheets

OTHER PUBLICATIONS

Mangelsdorf et al., "The Nuclear Receptor Superfamily: The Second Decade," Cell, 83:835–839 (1995).

Blumberg et al., "Orphan nuclear receptors–new ligands and new possibilities," Genes & Development, 12:3149–3155 (1998).

Burch et al., "Two Functional Estrogen Response Elements Are Located Upstream of the Major Chicken Vitellogenin Gene," Molecular and Cellular Biology, 8(3):1123–1131 (1988).

Cara et al., HIV–1 Protein Expression from Synthetic Circles of DNA Mimicking the Extrachromosomal Forms of Viral DNA, J. Biol. Chem., 271(10):5393–5397 (1996).

Chalfie et al., "Green Fluorescent Protein as a Marker for Gene Expression," Science, 263:802–805 (1994).

Chen et al., "Calcium Phosphate–Mediated Gene Transfer: A Highly Efficient Transfection System for Stably Transforming Cells with Plasmid DNA," BioTechniques, 6(7):632–638 (1988).

da Silva et al., "The nuclear hormone–receptor family in the brain: classics and orphans," TINS, 18(12):542–548 (1995).

* cited by examiner

SEQUENCE LISTING

<160> NUMBER OF SEQ ID NOS: 6

<210> SEQ ID NO 1
<211> LENGTH: 13

```
<212> TYPE: DNA
<213> ORGANISM: Artificial Sequence
<220> FEATURE:
<223> OTHER INFORMATION: Description of Artificial Sequence:FXR response
      element

<400> SEQUENCE: 1
aggtcaatga cct                                                          13

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:primer
      CYP7--78

<400> SEQUENCE: 2
tgatttgggg gattgctata                                                   20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:primer
      CYP7--178

<400> SEQUENCE: 3
catacctggg ctgtgctct                                                    19

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:primer
      CYP7--132(FAM)
<221> NAME/KEY: modified_base
<222> LOCATION: (1)
<223> OTHER INFORMATION: n = t modified by (6-FAM)
<221> NAME/KEY: modified_base
<222> LOCATION: (24)
<223> OTHER INFORMATION: n = t modified by (TAMRA)

<400> SEQUENCE: 4
nggttcaccc gtttgccttc tccn                                              24

<210> SEQ ID NO 5
<211> LENGTH: 8
<212> TYPE: PRT
<213> ORGANISM: Artificial Sequence
<220> FEATURE:
<223> OTHER INFORMATION: Description of Artificial
      Sequence:rhodamine-labeled receptor-interacting
      domain of coactivator SRC-1 peptide

<400> SEQUENCE: 5

Ile Leu Arg Lys Leu Leu Gln Glu
 1               5

<210> SEQ ID NO 6
<211> LENGTH: 201
<212> TYPE: PRT
<213> ORGANISM: Artificial Sequence
<220> FEATURE:
<223> OTHER INFORMATION: Description of Artificial Sequence:flexible
      linker
<221> NAME/KEY: MOD_RES
```

```
<222> LOCATION: (1)..(97)
<223> OTHER INFORMATION: Gly at positions 1-97 may be present or absent
<221> NAME/KEY: MOD_RES
<222> LOCATION: (105)..(201)
<223> OTHER INFORMATION: Gly at positions 105-201 may be present or
      absent

<400> SEQUENCE: 6

Gly Gly Gly Gly Gly Gly Gly Gly Gly Gly Gly Gly Gly Gly Gly Gly
  1               5                   10                  15

Gly Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
             85                  90                  95

Gly Gly Gly Gly Pro Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly Gly
        180                 185                 190

Gly Gly Gly Gly Gly Gly Gly Gly Gly
    195                 200
```

FXR RECEPTOR-MEDIATED MODULATION CHOLESTEROL METABOLISM

CROSS-REFERENCE TO RELATED APPLICATIONS

This application claims benefit of U.S. Provisional Patent Application No. 60/115,249, which was filed on Jan. 7, 1999, which application is incorporated herein by reference for all purposes.

BACKGROUND OF THE INVENTION

1. Field of the Invention

This invention relates to methods and compounds for the modulation of cholesterol metabolism in a mammal and methods for screening to identify candidate therapeutic agents for modulation of cholesterol levels.

2. Background

Atherosclerosis is a leading cause of death, myocardial infarctions, stroke, peripheral vascular disease and cardiovascular disease (Libby, in Chapter 242 of *Harrison's Principles of Internal Medicine*, 14th edition (1998) (Fauci et al., eds.); Witztum, in Chapter 36 of Goodman & Gilman's *The Pharmacological Basis of Therapeutics*, 9th edition (1996) (Hardman et al., eds.)). One of the major contributing factors to atherosclerosis is hypercholesterolemia. Hypercholesterolemia is currently treated with a combination of dietary and pharmaceutical therapies. Often more than a single pharmaceutical agent and a dietary regimen are necessary to decrease total cholesterol and LDL cholesterol levels to the desired level. Drugs such as bile acid sequestrants, niacin and the statins are commonly used to treat hypercholesterolemia and atherosclerosis. The use of niacin, however, is limited by the high incidence (>50%) of numerous side effects that are experienced in patients. Thus, a need for therapeutic agents that would decrease cholesterol levels still exists.

Cholesterol homeostasis in mammals is maintained through the coordinate regulation of three major pathways in the liver. Two pathways supply cholesterol to cells and include an endogenous biosynthetic pathway in which acetate is converted into cholesterol and an exogenous pathway in which members of the low-density lipoprotein receptor family bind and internalize cholesterol-carrying particles from the blood. A third pathway involves the conversion of cholesterol into hydrophilic bile acids.

The conversion of cholesterol to bile acids involves a minimum of fourteen enzymes of the bile acid biosynthetic pathway. The first and rate-limiting enzymatic reaction of this pathway is catalyzed by the enzyme cholesterol 7α-hydrolase. The cholesterol 7α-hydrolase gene, also known as cyp7A, belong to the cytochrome P-450 family that contains many microsomal enzymes involved in liver metabolism. It has been shown that expression of the cyp7A gene is tightly regulated. This gene is expressed exclusively in the liver and its expression can be induced by dietary cholesterol and suppressed by bile acids. An alternative pathway involves the cyp7B gene, which is expressed in the brain as well as other tissues. It has been shown that cholesterol catabolism plays a central role in cholesterol homeostasis. For instance, treatment of laboratory animals with cholestid or cholestyramine, two bile acid-binding resins, decreases serum cholesterol levels. Moreover, overexpression of the cyp7 gene in hamsters reduces both total cholesterol levels and LDL cholesterol levels. As such, cholesterol 7α-hydrolase is a potential therapeutic target for the identification of cholesterol reducing compounds and, thus, understanding the mechanism by which expression of the cyp7 genes are regulated is of particular importance.

Nuclear receptors form a large family of ligand-activated transcription factors that modify the expression of target genes by binding to specific cis-acting sequences (Laudet et al. (1992) *EMBO J.* 11: 1003–1013; Lopes da Silva et al. (1995) *Trends Neurosci.* 18: 542–548; Mangelsdorf et al. (1995) *Cell* 83: 835–839; Mangelsdorf and Evans (1995) *Cell* 83: 841–850). Nuclear receptors include those that remain sequestered in the cytoplasm in the absence of their cognate ligands (e.g., steroid hormone receptors). Upon binding of the ligand, the steroid hormone receptors are translocated to the nucleus where they bind to hormone response elements, typically as homodimers.

Most of the nuclear receptors, conversely, are not sequestered in the cytoplasm in the absence of their ligands but rather remain in the nucleus. These receptors, which include the thyroid hormone, retinoid, fatty acid, and eicosanoid receptors, typically bind to their cognate response elements as heterodimers with a 9-cis-retinoic acid receptor (RXR). Often, binding of a nuclear receptor to a response element occurs in the absence of the cognate ligand.

One such nuclear receptor is the farnesoid X receptor (FXR; also known as "RIP 14" and "NR1H4") (Forman et al. (1995) *Cell* 81: 687; Seol et al. (1995) *Mol. Endocrinol.* 9: 72; Mangelsdorf and Evans, supra.). FXR functions as a heterodimer with RXR, and several isoprenoid lipids can weakly activate FXR at supraphysiological concentration; however, these compounds do not activate all species of FXR and do not bind as ligands (Forman et al., supra.; Zavacki et al. (1997) *Proc. Nat'l. Acad. Sci.* USA 94: 7909). Thus, the identity and physiologic function of FXR ligands have remained unknown.

The lack of understanding of physiological mechanisms that regulate cholesterol levels has hampered the discovery of improved methods of treating hypercholesteremia. Thus, a need exists for characterization of regulatory mechanisms of cholesterol hemostasis, and for screening methods to identify better compounds for treating hypercholesteremia. The present invention fulfills these and other needs.

SUMMARY OF THE INVENTION

The present invention is based in part on the discovery that the orphan nuclear receptor FXR (farnesoid X receptor) is involved in the suppression of the human cyp7 genes. More particularly, it has been discovered that FXR functions as a bile acid receptor/sensor that mediates cyp7 expression in a bile-acid dependent manner. As such, in one aspect, the present invention provides a method for increasing cholesterol metabolism in a cell by contacting the cell with a compound that modulates the binding of an FXR to a ligand for FXR. In one embodiment, the ligand is a bile acid. In another embodiment, the compound modulates the binding of the FXR to an RXR or other coactivator or corepressor.

The invention provides methods for prescreening to identify a candidate therapeutic compound suitable for testing for ability to modulate cholesterol metabolism in a cell. These methods involve:

providing a reaction mixture that comprises:
    a) a polypeptide that comprises a ligand binding domain of an FXR;
    b) a ligand for FXR; and
    c) a test compound; and determining whether the amount of binding of the FXR ligand binding domain to the ligand for FXR is increased or decreased in the presence of the test compound compared to the amount of binding in the absence of the test compound. A test compound that causes an increase or decrease in binding is a candidate therapeutic agent for modulation of cholesterol metabolism. In some embodiments, the methods further involve administering the candidate therapeutic agent to a cell to determine whether the candidate therapeutic agent modulates cholesterol metabolism in the cell.

The invention also provides methods for screening to identify a compound that modulates cholesterol metabolism in a cell using a gene expression assay. For example, these methods can involve contacting a cell with a test compound, wherein said cell includes:

a) a polynucleotide that encodes a polypeptide comprising: 1) a DNA binding domain of a receptor which binds to DNA; and 2) a ligand binding domain that is substantially identical to a ligand binding domain of a FXR;

b) a ligand for FXR; and c) a reporter gene construct which comprises a response element to which said DNA binding domain can bind, wherein said response element is operably linked to a promoter that is operative in the cell and said promoter is operably linked to a reporter gene.

By determining whether the reporter gene is expressed at a higher or lower level in the presence of said test compound compared to said reporter gene expression level in the absence of said test compound, one can identify a test compound that can modulate cholesterol metabolism in a cell. The cells used in the methods of the invention are typically mammalian cells. In a presently preferred embodiment, the cell is in a mammal and, in particular, in a human.

The test compounds are, in some embodiments, a compound that binds to FXR or to the ligand for FXR, and thus inhibits binding of the ligand to the FXR. For example, the compound can be an antibody that binds to FXR, or an organic molecule that interferes with the interaction. The binding of the compound can also modulate the binding of a transcription complex that comprises FXR to a response element. Response elements of particular interest include those that are derived from a region upstream of a cyp7 gene.

In another embodiment, the present invention provides a method for reducing cholesterol levels in a mammal. These methods involve administering to said mammal a compound that modulates the binding of an FXR to an FXR response element. In a preferred embodiment, the mammal is a human.

The invention also provides assays for identifying ligands for FXR, and response elements that are bound by FXR or by a transcription complex that includes FXR.

BRIEF DESCRIPTION OF THE DRAWINGS

FIG. 1A illustrates that a GAL4 DNA binding domain fused to an FXR ligand binding domain is activated by CDCA, while ligand binding domains of other nuclear receptors fused to the GAL4 DBD are not activated by CDCA. FIG. 1B illustrates that CDCA-mediated transactivation of FXR is dose-dependent.

FIG. 2A illustrates that CDCA-mediated suppression of cyp7 is specific to FXR. FIG. 2B illustrates a dose-response profile of CDCA-mediated suppression of cyp7 expression by FXR.

FIG. 3A illustrates that FXR does not suppress expression of the low density lipoprotein (LDL) receptor. FIG. 3B illustrates that titrating away FXR causes a loss of cyp7 suppression. FIG. 3C illustrates that FXR mutants do not suppress cyp7 expression.

FIG. 4A illustrates a western blot analysis of cyp7 expression, as well as a quantitative RT-PCR analysis of cyp7 mRNA in HepG2 cells. FIG. 4B illustrates that FXR interacts with the co-activator SRC-1 in a mammalian two-hybrid assay. FIG. 4C shows the effect of different bile acids on FXR-mediated transactivation. FIG. 4D shows the effect of the bile acids on FXR-mediated suppression of cyp7 expression.

DETAILED DESCRIPTION

Figure 1A:
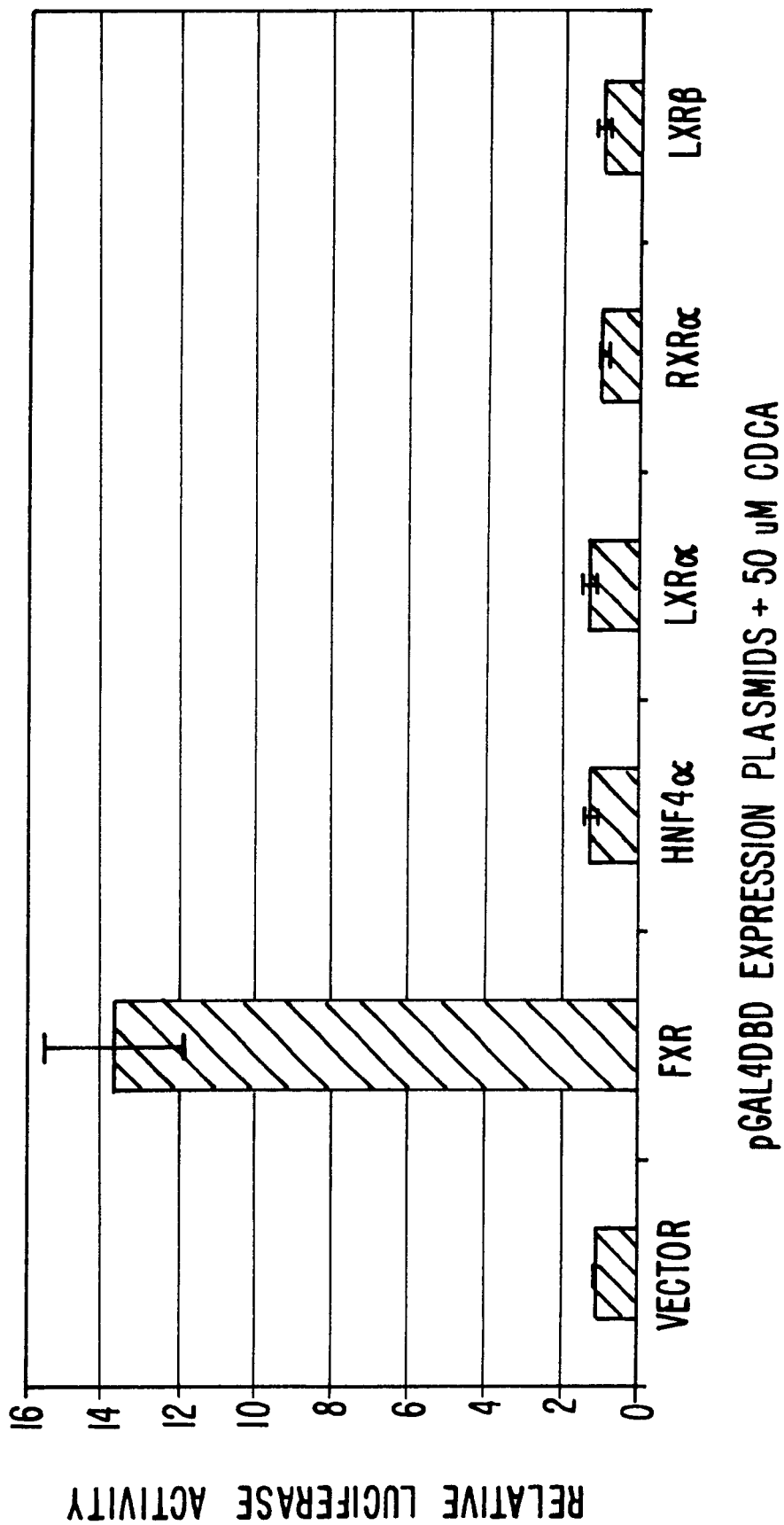
FIGS. 1A and 1B illustrate that the bile acid CDCA specifically transactivates FXR.

The following definitions are used herein.

Definitions

The term "isolated" refers to material that is substantially or essentially free from components which normally accompany the enzyme as found in its native state. Thus, the polypeptides of the invention do not include materials normally associated with their in situ environment. Typically, isolated proteins of the invention are at least about 80% pure, usually at least about 90%, and preferably at least about 95% pure as measured by band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual alignment and inspection.

The phrase "substantially identical," in the context of two nucleic acids or polypeptides, refers to two or more sequences or subsequences that have at least 75%, preferably 35%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions and/or untranslated regions.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M $Na^+$, typically about 0.01 to 1.0 M $Na^+$ concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The phrase "specifically or selectively binds to an antibody" or "specifically immunoreactive with", when referring to a protein or peptide, refers to a binding reaction which is determinative of the presence of the protein in the presence of a heterogeneous population of proteins and other biologics. Thus, under designated assay conditions, the specified antibodies or other ligand bind to a particular protein and do not bind in a significant amount to other proteins present in the sample. Specific binding to an antibody under such conditions may require an antibody that is selected for its specificity for a particular protein. For example, antibodies raised to the FXR polypeptides (or subsequences thereof) or to the polypeptides partially encoded by the FXR polynucleotide sequences can be selected to obtain antibodies specifically immunoreactive with the full length proteins and not with other proteins, except perhaps to polymorphic variants. A variety of immunoassay formats can be used to select antibodies and other molecules that specifically bind to a particular protein such as FXR. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity. Typically a specific or selective reaction will be at least twice background signal or noise and more typically more than 10 to 100 times background.

Description of the Preferred Embodiments

The present invention pertains to the discovery that ligands for the formerly orphan receptor FXR include bile acids, and that the binding of a bile acid to FXR results in suppression of cholesterol catabolism. Accordingly, the invention provides methods for modulating (i.e., increasing or decreasing) cholesterol levels in a cell by contacting the cell with a compound that modulates the binding of FXR to ligand for FXR. By decreasing binding of the FXR to an FXR ligand, for example, a compound can reduce the suppression of a gene such as cyp7 (i.e., increase the expression) which encodes an enzyme that is a key enzyme in cholesterol metabolism. Also provided by the invention are methods for increasing or decreasing cholesterol levels in a mammal, including humans by administering to the mammal a compound that modulates the binding of FXR to an FXR ligand. In other embodiments, the invention provides methods for identifying compounds that can modulate cholesterol metabolism by, for example, altering the ability of FXR to bind to FXR ligands.

A. Assays for Identifying Compounds that Modulate Cholesterol Metabolism

The invention also provides screening assays for identifying compounds that can modulate cholesterol metabolism. These compounds can function by, for example, altering the interaction between FXR and FXR ligands (e.g., bile acids, corepressors and/or coactivators) and/or between FXR and its response elements. Of particular interest is the modulation of cyp7 gene expression, which is inhibited by binding of FXR to the upstream region of the gene. Thus, a compound that inhibits the cis-repressing activity of FXR can increase the expression of cyp7, thus increasing degradation of cholesterol. Compounds that are identified using the screening methods of the invention find use in studies of gene regulation, and also find therapeutic use in situations in which it is desirable to increase or decrease cholesterol metabolism. Other uses will also be apparent those of ordinary skill in the art.

The assays of the invention are amenable to screening of large chemical libraries by automating the assay steps and providing compounds from any convenient source to assays, which are typically run in parallel (e.g., in microtiter formats on microtiter plates in robotic assays). Essentially any chemical compound can be used as a potential FXR activity modulator in the assays of the invention. In some embodiments, compounds that can be dissolved in aqueous or organic (especially DMSO-based) solutions are used. It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial library containing a large number of potential therapeutic compounds (potential modulator compounds). Such "combinatorial chemical libraries" are then screened in one or more assays, as described herein, to identify those library members (particular chemical species or subclasses) that display a desired characteristic activity (e.g., inhibit the interaction between FXR and an FXR ligand). The compounds thus identified can serve as conventional "lead compounds" or "candidate therapeutic agents," or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville, Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

The invention provides both biochemical and cell-based assays for identifying compounds that can modulate FXR-mediated regulation of cholesterol metabolism. Often, an initial assay is performed in vitro to identify compounds that are potential candidate therapeutic agents, after which such compounds are then tested in vivo by, for example, administering the compound to a test animal to determine whether cholesterol levels are affected.

1. Direct and Displacement Assays

The invention provides methods for identifying compounds that are suitable for further testing as candidate therapeutic agents for treatment of hypercholesteremia and other conditions that are associated with cholesterol synthesis and metabolism. Compounds that exhibit the desired activity in the in vitro assays can be used for further studies of the regulation of pathways involved in cholesterol hemostasis, or can be subjected for further testing to identify those that are suitable for use to treat hypercholesterolemia or other conditions involving cholesterol metabolism.

One type of assay that can be used is a direct binding assay, which measures the amount of a compound that can bind to an FXR polypeptide or to a polypeptide that has an FXR ligand binding domain. These assays can be carried out using labeled candidate therapeutic agents which are then incubated with a polypeptide that has an FXR ligand binding domain (e.g., a full-length FXR polypeptide or a fusion protein). Labels include radioisotopes, immunochemicals, fluorophores, and the like. Those of skill in the art will recognize a variety of ways of separating the bound labeled candidate therapeutic agent from the free labeled candidate therapeutic agent. The affinity of the labeled candidate therapeutic agent for an FXR polypeptide can be calculated using standard ligand binding methods.

Another type of assay that can be used to pre-screen candidate therapeutic agents involves testing the ability of a test compound to modulate binding of FXR to a ligand for FXR. These can be conducted, for example, as a direct binding assay with a labeled FXR ligand in the presence of a candidate therapeutic agent. The assays involve placing the test compound into an assay mixture that includes at least a ligand binding domain of an FXR polypeptide and a ligand for FXR. The effect on binding of the FXR ligand to FXR is determined. A test compound that decreases the amount of labeled FXR ligand that is bound to an FXR polypeptide or a polypeptide that has an FXR ligand binding domain, is of interest for future screening for its ability to modulate cholesterol levels in vivo.

Ligands that are suitable for use in the assays of the invention include, but are not limited to, bile acids and related compounds such as CDCA (chenodeoxycholic acid), GCDCA (glycochenodeoxycholic acid), TCDCA (taurochenodeoxycholic acid), GCA (glycocholic acid), TCA (taurocholic acid), DCA (deoxycholic acid), LCA (lithocholic acid), DHCA (dehydrocholic acid), UDCA (ursodeoxycholic acid) and CA (cholic acid). In a presently preferred embodiment, the bile acid is CDCA. Additional bile acids and other ligands are described in, for example, Makishima et al. (1999) *Science* 284: 1362–1365. The assays can also employ coactivators and corepressors with which FXR interacts. Methods of identifying FXR ligands are described below.

In presently preferred embodiments, an assay such as the fluorescence polarization assay or the fluorescence resonance energy transfer assay is employed to identify candidate therapeutic agents. These assays do not require the separation of bound and free labeled test compound. Fluorescence polarization (FP) or fluorescence anisotropy is a useful tool for the study of molecular interactions (see, e.g. http://www.panvera.corn/tech/appguide/fpintro.html, Nov. 4, 1999). First, a molecule labeled with a fluorophore is excited with plane polarized light. If the fluorescent molecule stays stationary while in the excited state, light is emitted in the same polarized plane. If the excited fluorescently labeled molecule rotates out of the plane of the polarized light while in the excited state, light is emitted from the molecule in a different plane. For example, if vertical polarized light is used to excite the fluorophore, the emission spectra can be monitored in the vertical and horizontal planes. Fluorescence polarization is calculated as shown in the following Formula I:

$$\text{Fluorescent polarization} = P = (\text{Int}\|-\text{Int}\bot)/(\text{Int}\|+\text{Int}\bot)\text{I}$$

In Formula I, Int $\|$ is the intensity of the emission parallel to the excitation plane. Int$\bot$ is the intensity of the emission perpendicular to the excitation plane.

A small fluorescently labeled molecule, when free in solution, can emit depolarized light when excited with the proper wavelength of light. If, however, the molecule (e.g., a ligand) binds to a second molecule (e.g., a receptor) the fluorescently labeled molecule is more constrained so the light emitted is more polarized and the fluorescence polarization (FP) value is higher. Thus, a higher FP value indicates that the fluorescently labeled molecule is able to bind to the second molecule. A competition assay also can be performed using FP. If an unlabeled molecule is present in the solution, then it will compete for binding to the second molecule, e.g., the antibody and the FP value will be decreased. Thus, FP can be used in competitive assays.

Commercial assays exist to test the affinity of compounds for human estrogen receptor α and β using a fluorescently labeled estrogen compound (see, Panvera, (Madison, Wis.) publications Lit.#'s L0069, L0082, L0084, L0095, L0072, L0085). Similarly, test compounds can be fluorescently labeled with a fluorophore that is active in a FP assay. For example, N-terminal amines of proteins, peptide, or peptide analogs can be labeled with fluorescein (Panvera, publications Lit. # L0057 and L0059) or a small fluorescent compound. Briefly, a fluorescein-$C_6$-succinimidyl ester can be conjugated to peptides or proteins. The fluorescein labeled peptide/protein can then be purified from the unreacted fluorescein-C6-succinimidyl ester using thin-layer chromatography or gel filtration chromatography. If the labeled test compound can bind to a polypeptide that has an FXR ligand binding domain, the level of polarization is increased. The FP assay also can be used to assay the ability of a fluorescently labeled FXR ligand to bind to an FXR polypeptide.

Alternatively, a test compound can be screened for its ability to decrease the FP of a fluorescently labeled known FXR ligand complexed with an FXR polypeptide or a polypeptide comprising an FXR ligand binding domain. Briefly, a known FXR ligand is labeled with a fluorescent moiety. A test compound that decreases the FP value of the fluorescently labeled FXR ligand and FXR is displacing or inhibiting the ability of the fluorescently labeled FXR ligand to bind to the ligand binding domain of FXR.

Methods employing the technique of fluorescence resonance energy transfer (FRET) can be employed using the methods and compositions of the present invention. FRET occurs between two fluorophores when the excitation of the donor fluorophore is transferred to the acceptor fluorophore. This interaction is dependent on the distance between the donor and acceptor fluorophore and distance-dependent interaction between a donor and acceptor molecule. The donor and acceptor molecules are fluorophores. If the fluorophores have excitation and emission spectra that overlap, then in close proximity (typically around 10–100 angstroms) the excitation of the donor fluorophore is transferred to the acceptor fluorophore. The relative proximity of the first and second labels is determined by measuring a change in the intrinsic fluorescence of the first or second label. Commonly, the emission of the first label is quenched by proximity of the second label.

Many appropriate interactive labels for FRET are known. For example, fluorescent labels, dyes, enzymatic labels, and antibody labels are all appropriate. Examples of preferred interactive fluorescent label pairs include terbium chelate and TRITC (tetrarhodamine isothiocyanate), europium cryptate and allophycocyanin and many others known to one of skill. Similarly, two colorimetric labels can result in combinations that yield a third color, e.g., a blue emission in proximity to a yellow emission produces an observed green emission.

With regard to preferred fluorescent pairs, there are a number of fluorophores which are known to quench each other. Fluorescence quenching is a bimolecular process that reduces the fluorescence quantum yield, typically without changing the fluorescence emission spectrum. Quenching can result from transient excited interactions, (collisional quenching) or, e.g., from the formation of nonfluorescent ground state species. Self-quenching is the quenching of one fluorophore by another; it tends to occur when high concentrations, labeling densities, or proximity of labels occurs. Some excited fluorophores interact to form excimers, which are excited state dimers that exhibit altered emission spectra (e.g., phospholipid analogs with pyrene sn-2 acyl chains); See Haugland (1996) *Handbook of Fluorescent Probes and Research Chemicals*, published by Molecular Probes, Inc., Eugene, Oreg.

The Forster radius ($R_o$) is the distance between fluorescent pairs at which energy transfer is 50% efficient (i.e., at which 50% of excited donors are deactivated by FRET). The magnitude of is dependent on the spectral properties of donor and acceptor dyes: $R_o = [8.8 \times 10^{23} \cdot K^2 \cdot n^{-4} \cdot QY_D \cdot J(\lambda)]^{1/6}$ Å; where $K^2$ = dipole orientation range factor (range 0 to 4, $K^2 = 2/3$ for randomly oriented donors and acceptors).; $QY_D$ = fluorescence quantum yield of the donor in the absence of the acceptor; n = refractive index; and J($\square$)= spectral overlap integral=$\int \epsilon_A(\lambda) \cdot F_D \cdot (\lambda 4) d\lambda \text{cm}^3 \text{M}^{-1}$, where $\epsilon_A$ = extinction coefficient of acceptor and FD = fluorescence emission intensity of donor as a fraction of total integrated intensity. Some typical $R_o$ are listed for typical donor acceptor pairs in Table 1:

TABLE 1

| Donor | Acceptor | $R_o$ (Å) |
| --- | --- | --- |
| Fluorescein | Tetramethylrhodamine | 55 |
| IAEDANS | Fluorescein | 46 |
| EDANS | DABCYL | 33 |
| BODIPY FL | BODIPY FL | 57 |
| Fluorescein | QSY-7 dye | 61 |

An extensive compilation of $R_o$ values are found in the literature; see Haugland (1996), supra. In most uses, the donor and acceptor dyes are different, in which case FRET can be detected by the appearance of sensitized fluorescence of the acceptor or by quenching of the donor fluorescence. When the donor and acceptor are the same, FRET is detected by the resulting fluorescence depolarization.

In addition to quenching between fluorophores, individual fluorophores are also quenched by nitroxide-labeled molecules such as fatty acids. Spin labels such as nitroxides are also useful in the liquid phase assays of the invention.

Test compounds and a polypeptide that includes an FXR ligand binding domain can be labeled with FRET pairs. If the test compound can directly interact with the FXR ligand binding domain, fluorescence resonance energy transfer can take place and the affinity can be measured. Alternatively, a known FXR ligand can be labeled with an appropriate FRET label and incubated with an FRET fluorophore labeled polypeptide that includes an FXR ligand binding domain. Fluorescence resonance energy transfer can take place between the labeled FXR ligand and the labeled FXR ligand binding domain. If a test compound were incubated with the two labeled components, the amount of FRET would be lowered if the test compound can inhibit or displace the binding of the labeled FXR ligand to the FXR ligand binding domain.

Additional methods for assaying the ability of test compounds to modulate FXR interactions with its ligands employ peptide sensors. These assays can be adapted from those described in WO 99/27365. Briefly, these assays use a peptide sensor to which is attached a detectable label. The peptides are based on corepressor or coactivator protein motif sequences, either naturally occurring or derived from mutational analysis. The peptide sensors are derived from corepressors or coactivators that interact with FXR (e.g., a p160 coactivator, RXR, CPF, and others that are identified as described herein). Alternatively, the peptides can be obtained through randomizing residues and selecting for binding to the FXR receptor polypeptide. Panels of predetermined or randomized candidate sensors can be screened for receptor binding. For FXR peptide sensor assays, an example of a suitable peptide sensor is derived from the receptor-interacting domain of the coactivator SRC-1. This domain has been mapped to a short motif with the amino acid sequence LXXLL, where L is leucine and X is any amino acid. Fragments of SRC-1 or short synthetic peptides containing one LXXLL motif or more bind nuclear receptors in a ligand-dependent manner (Darimont et al. (1998) *Genes Dev.* 12: 3343; McInerney et al. (1998) *Genes Dev.* 12: 3357).

In typical embodiments, the sensor peptides are labeled with a detectable label. The detectable labels can be primary labels (where the label comprises an element that is detected directly or that produces a directly detectable element) or secondary labels (where the detected label binds to a primary label, as is common in immunological labeling). An introduction to labels, labeling procedures and detection of labels is found in Polak and Van Noorden (1997) *Introduction to Immunocytochemistry*, 2nd ed., Springer Verlag, N.Y. and in Haugland (1996) *Handbook of Fluorescent Probes and Research Chemicals*, a combined handbook and catalogue published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., 3H, 125I, 35S, 14C, 32P, 33P, etc.), enzymes (e.g., horse radish peroxidase, alkaline phosphatase etc.), spectral colorimetric labels such as colloidal gold or colored glass or plastic (e.g., polystyrene, polypropylene, latex, etc.) beads. The label may be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions. In a presently preferred embodiment, the detectable label is a fluorescent label, in which case fluorescence polarization detection provides a sensitive and efficient means of detecting whether the peptide sensor is bound to the FXR receptor polypeptide. See, e.g., Schindler et al. (1995) *Immunity* 2: 689–697).

The sensor peptide and the FXR polypeptide are incubated under conditions that are suitable for sensor binding to the receptor polypeptide. In some embodiments, a candidate modulator of FXR binding to a corepressor, coactivator or other ligand is included in the reaction mixture. If a candidate modulator increases or decreases binding of the sensor peptide to the FXR polypeptide, the candidate modulator is a potential lead compound for blocking the FXR-mediated effect on transcription.

2. Cell-based Screening Methods

The present invention also provides cell-based methods for screening to identify compounds that are suitable for use as cholesterol level-mediating therapeutic agents, or that are suitable to further screening compounds that exhibit activity in the polypeptide-based assays described above. These methods provide an assay to determine whether expression of a gene involved in cholesterol hemostasis is affected by administration of the test compound.

In some embodiments, these screening methods of the invention use a cell that contains a polypeptide that has a ligand binding domain (LBD) which is at least substantially identical to that of an FXR. The polypeptide typically will also include a DNA binding domain (DBD). The DBD can be substantially identical to that of an FXR (i.e., a full-length FXR is used), or to that of a receptor other than FXR for which the response element is known (e.g., GAL4, nuclear hormone receptors, and the like). Examples of suitable chimeric polypeptides are described in more detail below. Conveniently, the chimeric receptor polypeptide is introduced into the cell by expression of a polynucleotide that encodes the receptor polypeptide. For example, an expression vector that encodes the chimeric receptor can be introduced into the cell that is to be used in the assay. Suitable FXR polypeptides and chimeric receptors are described below.

The cells will also contain a response element that can be bound by the DNA binding domain. Response elements, including glucocorticoid response elements (GRE) and estrogen response elements (ERE), are described in, for example, Jantzen et al. (1987) *Cell* 49: 29; Martinez et al. (1987) *EMBO J.* 6: 3719 and Burch et al. (1988) *Mol. Cell. Biol.* 8: 1123. Many other response elements are known; a commonly used response element is the GAL4 upstream activating sequence ($UAS_G$) (Keegan et al. (1986) *Science* 14: 699–704), which is responsive to binding by chimeric receptors that include the GAL4 DNA binding domain.

The response element that is bound by the DNA binding domain used in the chimeric polypeptide is generally used in a reporter gene construct. In such constructs, the response element is operably linked to a promoter that is active in the cell. In presently preferred embodiments, the promoter is operably linked to a reporter gene that, when expressed, produces a readily detectable product. The response element/reporter gene construct is conveniently introduced into cells as part of a "reporter plasmid."

Suitable promoters include those described above. In presently preferred embodiments, the promoter is operably linked to a reporter gene that, when expressed, produces a readily detectable product. A variety of reporter gene plasmid systems are known, such as the chloramphenicol acetyltransferase (CAT) and β-galactosidase (e.g., bacterial lacZ gene) reporter systems, the firefly luciferase gene (See, e.g., Cara et al. (1996) *J. Biol. Chem.*, 271: 5393–5397), the green fluorescence protein (see, e.g., Chalfie et al. (1994) Science 263:802) and many others. Examples of reporter plasmids are also described in U.S. Pat. No. 5,071,773. Selectable markers which facilitate cloning of the vectors of the invention are optionally included. Sambrook and Ausubel, both supra, provide an overview of selectable markers.

In some embodiments of this assay, the reporter plasmid and an expression plasmid that directs expression of the chimeric receptor are introduced into a suitable host cell. Standard transfection methods can be used to introduce the vectors into the host cells. For mammalian host cells, preferred transfection methods include, for example, calcium phosphate precipitation (Chen and Okayama (1988) *BioTechniques* 6: 632), DEAE-dextran, and cationic lipid-mediated transfection (e.g., Lipofectin) (see, e.g., Ausubel, supra.). In some cases, the host cell, prior to introduction of the expression plasmid, should not contain an FXR receptor. See, e.g., U.S. Pat. No. 5,071,773 for suitable host cells for use in the assays.

The assay methods involve contacting test cells that contain the reporter plasmid, the native or chimeric FXR polypeptide, and a ligand (e.g., bile acid) with the test compound. In some embodiments, an RXR polypeptide and/or other coactivators and corepressors which mediate the effect of FXR are also present in the test cells. For example, a cell that contains a reporter gene construct and the chimeric peptide can be grown in the presence and absence of putative modulatory compounds.

The observed effect on reporter gene expression can depend on the particular assay system used. For example, when an FXR polypeptide that includes the FXR DBD, AF-2 domain, and LBD is used, cells grown in the absence of the FXR ligand will exhibit a level of reporter gene expression that is above the level observed in the absence of the ligand. Conversely, when a GAL4 DBD is used, binding of the ligand to the fusion polypeptide will result in increased expression the reporter gene to which is linked the GAL4 response element. Therefore, reporter gene expression is increased when cells are grown in the presence of a ligand for the FXR.

B. FX Polypeptides and Fusion Polypeptides

The assays of the invention typically employ an FXR polypeptide. The FXR polypeptide can be a full-length FXR, or can include one or more domains of FXR. In some embodiments, one or more FXR domains (e.g., a DNA binding domain (DBD) or a ligand binding domain (LBD)) are used as a fusion protein with a domain from another polypeptide, such as another receptor. For example, some assay formats use a fusion protein that includes an FXR LBD fused to a DBD of another receptor.

The FXR polypeptides and fusion polypeptides used in the assays of the invention can be made by methods known to those of skill in the art. For example, the FXR proteins or subsequences thereof can be synthesized using recombinant DNA methodology. Generally this involves creating a DNA sequence that encodes the polypeptide, modified as desired, placing the DNA in an expression cassette under the control of a particular promoter, expressing the protein in a host, isolating the expressed protein and, if required, renaturing the protein.

FXR polypeptides, and polynucleotides that encode FXR polypeptides, are known to those of skill in the art. For example, cDNA sequences of FXR polypeptides from human (U68233), *Branchiostoma lanceolatum* (U93409), *Danio rerio* (zebrafish) (U93467), and rat (U18374) are found in GenBank. The nucleic acids that encode FXR can be used to express the FXR polypeptide, or to construct genes that encode a desired fusion polypeptide.

FXR-encoding nucleic acids can be isolated by cloning or amplification by in vitro methods, such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger, Sambrook, and Ausubel (all supra.); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al. (1987) U.S. Pat. No. 4,683,202; *PCR Protocols A Guide to Methods and Applications* (Innis et al., eds) Academic Press Inc. San Diego, Calif. (1990) (Innis); Amnheim & Levinson (October 1, 1990) C&EN 36–47; *The Journal Of NIH Research* (1991) 3: 81–94; (Kwoh et al. (1989) *Proc. Nat'l. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8:–291–294; Wu and Wallace (1989) *Gene*, 4: 560; and Barringer et al. (1990) Gene 89: 117.

In one preferred embodiment, FXR cDNAs can be isolated by routine cloning methods. The cDNA sequence provided in GenBank, for example, can be used to provide probes that specifically hybridize to a FXR gene in a genomic DNA sample, to an FXR mRNA in a total RNA sample, or to a FXR cDNA in a cDNA library (e.g., in a Southern or Northern blot). Once the target FXR nucleic acid is identified, it can be isolated according to standard methods known to those of skill in the art (see, e.g., Berger and Kimmel, Guide to *Molecular Cloning Techniques, Methods in Enzymology* 152 Academic Press, Inc., San Diego, Calif. (Berger); Sambrook et al. (1989) *Molecular Cloning-A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). In another preferred embodiment, the FXR nucleic acids can be isolated by amplification methods such as polymerase chain reaction (PCR).

A polynucleotide that encodes an FXR polypeptide or fusion protein can be operably linked to appropriate expression control sequences for a particular host cell in which the polypeptide is to be expressed. For *E. coli*, appropriate control sequences include a promoter such as the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1,10 (Johnson and Davies (1984) *Mol. Cell. Biol.* 4:1440–1448) ADH2 (Russell et al. (1983) *J. Biol. Chem.* 258:2674–2682), PHO5 (*EMBO J.* (1982) 6:675–680), and MFα1 (Herskowitz and Oshima (1982) in *The Molecular Biology of the Yeast Saccharomyces* (eds. Strathem, Jones, and Broach) Cold Spring Harbor Lab., Cold Spring Harbor, N.Y., pp. 181–209).

Expression cassettes are typically introduced into a vector which facilitates entry into a host cell, and maintenance of the expression cassette in the host cell. Vectors that include a polynucleotide that encodes an FXR polypeptide are provided by the invention. Such vectors often include an expression cassette that can drive expression of the FXR polypeptide. To easily obtain a vector of the invention, one can clone a polynucleotide that encodes the FXR polypeptide into a commercially or commonly available vector. A variety of common vectors suitable for this purpose are well known in the art. For cloning in bacteria, common vectors include pBR322 derived vectors such as pBLUESCRIP™, and λphage derived vectors. In yeast, vectors include Yeast Integrating plasmids (e.g., YIp5) and Yeast Replicating plasmids (the YRp series plasmids) and pGPD-2. A multicopy plasmid with selective markers such as Leu-2, URA-3, Trp-1, and His-3 is also commonly used. A number of yeast expression plasmids such as YEp6, YEp13, YEp4 can be used as expression vectors. The above-mentioned plasmids have been fully described in the literature (Botstein et al. (1979) *Gene* 8:17–24; Broach et al. (1979) *Gene*, 8:121–133). For a discussion of yeast expression plasmids, see, e.g., Parents, B., YEAST (1985), and Ausubel, Sambrook, and Berger, all supra). Expression in mammalian cells can be achieved using a variety of commonly available plasmids, including pSV2, pBC12BI, and p91023, as well as lytic virus vectors (e.g., vaccinia virus, adenovirus, and baculovirus), episomal virus vectors (e.g., bovine papillomavirus), and retroviral vectors (e.g., murine retroviruses).

FXR polypeptides and fusion polypeptides that include at least one FXR domain can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, *Gene Expression in Recombinant Microorganisms* (Bioprocess Technology, Vol. 22), Marcel Dekker, 1994. Examples of bacteria that are useful for expression include, but are not limited to, Escherichia, Enterobacter, Azotobacter, Erwinia, Bacillus, Pseudomonas, Klebsielia, Proteus, Salmonella, Serratia, Shigella, Rhizobia, Vitreoscilla, and Paracoccus. Filamentous fungi that are useful as expression hosts include, for example, the following genera: Aspergillus, Trichoderma, Neurospora, Penicillium, Cephalosporium, Achlya, Podospora, Mucor, Cochliobolus, and Pyricularia. See, e.g., U.S. Pat. No. 5,679,543 and Stahl and Tudzynski, Eds., Molecular Biology in Filamentous Fungi, John Wiley & Sons, 1992. Synthesis of heterologous proteins in yeast is well known and described in the literature. *Methods in Yeast Genetics*, Sherman, F., et al., Cold Spring Harbor Laboratory, (1982) is a well recognized work describing the various methods available to produce the enzymes in yeast.

The nucleic acids that encode the polypeptides of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes, among others. Techniques for transforming fungi are well known in the literature and have been described, for instance, by Beggs et al. ((1978) *Proc. Nat'l. Acad. Sci. USA* 75: 1929–1933), Yelton et al. ((1984) *Proc. Natl. Acad. Sci. USA* 81: 1740–1747), and Russell ((1983) *Nature* 301: 167–169). Procedures for transforming yeast are also well known (see, e.g., Beggs (1978) *Nature (London)*, 275:104–109; and Hinnen et al. (1978) *Proc. Natl. Acad. Sci. USA*, 75:1929–1933. Transformation and infection methods for mammalian and other cells are described in Berger, Sambrook, and Ausubel, supra.

Once expressed, the FXR polypeptides and/or fusion proteins can be purified, either partially or substantially to homogeneity, according to standard procedures of the art, such as, for example, ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Once purified, partially or to homogeneity as desired, the polypeptides may then be used (e.g., in screening assays for modulators for gene expression or as immunogens for antibody production).

One of skill in the art would recognize that after chemical synthesis, biological expression, or purification, the FXR polypeptides and/or fusion proteins may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065–14070; Kreitman and Pastan (1993) *Bioconjug Chem.*, 4: 581–585; and Buchner, et al., (1992) *Anal. Biochem.*, 205: 263–270). Debinski et al., for example, describe the denaturation and reduction of inclusion body proteins in guanidine-DTE. The protein is then refolded in a redox buffer containing oxidized glutathione and L-arginine.

One of skill also would recognize that some modifications can be made to the FXR polypeptides without diminishing their biological activity. Such modifications can be made to facilitate the cloning, expression, or incorporation of the polypeptide into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

C. Chimeric FXR Polypeptides

The assays of the invention sometimes employ a chimeric FXR polypeptide that has at least a ligand binding domain and a DNA binding domain. At least one of the ligand binding domain and the DNA binding domain of the chimeric receptors of the invention is substantially identical to the corresponding domain of an FXR. These chimeric receptors are useful for many purposes. For example, one can use the chimeric receptors to identify additional ligands for the FXR and to identify response elements that are responsive to FXR. The chimeric receptors are also useful in screening assays for identifying compounds that can modulate interactions between FXR and its ligands and/or response elements.

1. DNA Binding Domains.

The chimeric receptors used in the assays of the invention include those having a ligand binding domain that is at least substantially identical to a ligand binding domain of an FXR, as well as those that have a DNA binding domain that is not substantially identical to a DNA binding domain of an FXR. For example, the DNA binding domain binding domain can be about 90% or less identical to that of an FXR, more preferably about 75% or less, and most preferably about 60% or less identical. Often, the DNA binding domain is derived from a receptor other than a FXR. In a typical embodiment, the DNA binding domain is at least substantially identical to a DNA binding domain from a nuclear hormone receptor or a steroid hormone receptor.

The modular nature of transcription regulators facilitates the construction of chimeric receptors that have domains that are derived from different receptors (Green and Chambon (1986) *Nature* 324: 615–617). For example, DNA binding domains derived from steroid, thyroid, and retinoid hormone receptor are suitable for use in the chimeric receptors of the invention. The DNA binding domains of receptors for steroid, thyroid, and retinoid hormones typically include two zinc finger units (Rhodes and Klug (Feb. 1993) *Scientific American*, pp. 56–65). The DNA binding domains of these receptors, are generally cysteine-rich regions of about 65 amino acids that fold into two cysteine-rich "C4" type zinc fingers. The boundaries for many DNA binding domains have been identified and characterized for the steroid hormone superfamily. See, e.g., Giguere et al. (1986) *Cell* 46:645–652; Hollenberg et al. (1987) *Cell* 49:39–46; Green and Chambon (1987) *Nature* 325:74–78; Miesfield et al. (1987) *Science* 236:423–427; and Evans (1988) *Science* 240:889–895.

Examples of receptors from which one can derive DNA binding domains that are suitable for use in the chimeric receptors of the invention include, for example, androgen receptors, estrogen receptors, glucocorticoid receptors, mineralcorticoid receptors, progesterone receptors, retinoic acid receptors (including $\alpha$, $\beta$ (hap), and $\lambda$), thyroid hormone receptors (including $\alpha$ and $\beta$), the gene product of the avian erythroblastosis virus oncogene v-erbA (which is derived from a cellular thyroid hormone receptor), vitamin D3 receptor, Drosophila ecdysone receptor (EcR), COUP transcription factor (also known as ear3) and its Drosophila homolog 7UP (svp), hepatocyte nuclear factor 4 (HNF-4), Ad4BP, apolipoprotein AI regulatory protein-1 (ARP-1), peroxisome proliferator activated receptor (PPAR), Drosophila protein knirps (kni), Drosophila protein ultraspiracle (usp; chorion factor 1), human estrogen receptor related genes 1 and 2 (err1 and err2), human erbB related gene 2 (ear2), human NAK1/mouse nur/77 (N10)/rat NGFI-B; Drosophila protein embryonic gonad (egon), Drosophila knirps-related protein (knr1), Drosophila protein tailless (tll), Drosophila 20-O-ecdysone regulated protein E75, and Drosophila Dhr3. Some of these and other suitable receptors are described in, for example, Evans, RM (1988) *Science* 240: 889–895; Gehrig, U. (1987) *Trends Biochem. Sci*. 12: 399–402; Beato, M. (1989) *Cell* 56: 335–344; Laudet et al. (1992) *EMBO J*. 11: 1003–1013.

In some embodiments, the chimeric receptors include a DNA binding domain from a DNA-binding polypeptide other than a nuclear receptor. For example, chimeric receptors that have the DNA binding domain of GAL4, which is a positive regulatory protein of yeast (Giniger et al. (1985) *Cell* 40: 767–774; Sadowski et al. (1992) *Gene* 118: 137–141) linked to a ligand binding domain of an FXR polypeptide are provided. GAL4 DNA binding domain-containing fusion proteins can be readily expressed by cloning a coding sequence for an FXR ligand binding domain into a commercially available expression vector that includes a GAL4 DNA binding domain coding sequence under the control of a promoter (e.g., pAS2–1 (CLONTECH Laboratories, Inc.). Another example of a well-characterized DNA binding domain for which expression vectors are commercially available is that of LexA (pLexA, CLONTECH). The chimeric receptors can also include a nuclear localization sequence associated with the DNA binding domain (see, e.g., Silver et al. (1984) *Proc. Nat'l. Acad. Sci. USA* 81: 5951–5955 for a GAL4 nuclear localization sequence).

The chimeric receptors can use an entire receptor molecule as a DNA binding domain, or can use portions of molecules that are capable of binding to nucleic acids, directly or indirectly. To identify such DNA binding domains, one can perform assays such as an electrophoretic mobility shift assay (EMSA) (Scott et al. (1994) *J. Biol. Chem*. 269: 19848–19858), in which a nucleic acid of interest is allowed to associate with various fragments of a polypeptide to identify those fragments that are capable of binding to the nucleic acid. Association of a portion of the protein with the nucleic acid will result in a retardation of the electrophoretic mobility of the nucleic acid. Another method by which one can identify DNA binding moieties that are suitable for use as DNA binding domains is DNase I footprinting, which is well known to those of skill in the art.

The DNA binding domain can be either a polypeptide or a nucleic acid. Where the DNA binding domain is a nucleic acid, the nucleic acid will be capable of specifically hybridizing to a target nucleic acid site, such as a response element. Hybridization of the nucleic acid to the target site will place the chimeric receptor in a position suitable for activating or repressing expression of a gene that is linked to the target site. An example of an oligonucleotide being chemically linked to a protein by chemical coupling is found in Corey et al. (1989) *Biochemistry* 28: 8277–8286.

These chimeric receptors are useful, for example, in assays to identify modulators of FXR transcriptional regulation activity as described below.

2. Ligand Binding Domains.

The assays of the invention typically use chimeric or non-chimeric FXR receptors in which the ligand binding domain is at least substantially identical to a ligand binding domain of an FXR polypeptide.

3. Production of Chimeric FXR Receptors

To form a chimeric receptor for use in the assay of the invention, the ligand binding domain and the DNA binding domain are linked together. Suitable methods of forming such linkages are known to those of skill in the art. For a review of methods for constructing fusion proteins between receptor ligand binding domains and DNA binding domains, see, e.g., Mattioni et al. (1994) *Methods in Cell Biology* 43(Pt A): 335–352. The linkage can be done using either recombinant or chemical methods. For example, a cysteine residue can be placed at either end of a domain so that the domain can be linked to another domain by, for example, a sulfide linkage. More typically, the ligand binding domains and DNA binding domains are joined by linkers, which are typically polypeptide sequences, such as poly glycine sequences of between about 5 and 200 amino acids, with between about 10–100 amino acids being typical. In some embodiments, proline residues are incorporated into the linker to prevent the formation of significant secondary structural elements by the linker. Preferred linkers are often flexible amino acid subsequences which are synthesized as part of a recombinant fusion protein. In one embodiment, the flexible linker is an amino acid subsequence comprising a proline such as Gly(x)-Pro-Gly(x)(SEQ ID NO:6) where x is a number between about 3 and about 100. A linker can also be a single peptide bond, or one or more amino acid residues. In other embodiments, a chemical linker is used to connect synthetically or recombinantly produced ligand binding domain and DNA binding domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heteroflinctional linkages.

The chimeric receptors are conveniently produced by recombinant expression in a host cell. Accordingly, the invention provides chimeric nucleic acids that encode a fusion protein that includes a DNA binding domain and a ligand binding domain, at least one of which is at least substantially identical to the corresponding domain of an FXR of the invention. In some embodiments, the chimeric nucleic acid will also encode a linker region that provides a link between the two domains. Techniques for making such chimeric nucleic acids are known to those of skilled in the art. For example, recombinant methods can be used (see, e.g., Berger and Sambrook, both supra.). Alternatively, the nucleic acid encoding the chimeric receptors can be synthesized chemically.

To obtain expression of a chimeric receptor, a nucleic acid that encodes the chimeric receptor is generally placed under the control of a promoter and other control elements that can drive expression of the chimeric gene in a desired host cell. Accordingly, the invention also provides expression cassettes in which a promoter and/or other control elements are operably linked to a polynucleotide that encodes a chimeric receptor. Suitable promoters, other control sequences, and expression vectors are described above.

D. Assays for FXR Ligands and Response Elements

Also provided by the invention are methods for identifying corepressors, coactivators, and additional ligands that interact with FXR. Also provided are methods of identifying response elements that are mediated by transcription complexes that include FXR. These components are useful in the screening assays of the invention.

1. Identification of Ligands for FXR

Many of the screening assays of the invention utilize ligands for FXR. Accordingly, the invention provides methods for identifying additional ligands for FXR. The identification of previously unknown FXR ligands is of particular interest not only for the knowledge obtained regarding the regulation of cholesterol metabolism, but also for identifying new compounds that can modulate FXR-mediated regulation of genes that are involved in cholesterol metabolism.

Candidate ligands include not only bile acids and related compounds, but also transcription factors, coactivators, and corepressors with which FXR might interact. These potential ligands can include other receptor polypeptides (e.g., RXR, coactivators, and the like), which comprise the cellular machinery for regulation of gene expression. For example, nuclear hormone receptors often interact with transcriptional coactivators. Thus, the invention also provides methods of identifying coactivators, corepressors and other molecules that interact with FXRs. These assay methods can involve introducing a coactivator or a corepressor that is a candidate ligand for FXR into a host cell that contains a chimeric FXR and reporter plasmid. The coactivator can be introduced by means of an expression construct; this expression construct can be present on the same or a different vector than the expression construct for the chimeric receptor.

Ligands for FXR can be identified using the methods described above for screening to identify compounds that modulate FXR interactions with the ligands. Instead of including a compound that potentially modulates the interaction, the assays are conducted using a potential FXR ligand. Both polypeptide-based and cell-based assays can be used.

2. Identification of Response Elements for Transcription Complexes That Include FXR The present invention provides methods for obtaining response elements that are responsive to transcription complexes that include FXR. Through use of such methods, one can identify additional genes for which expression is modulated by the FXRs. The methods typically involve contacting a putative response element with a polypeptide that includes a FXR DNA binding domain (see, e.g., Ausubel et al., supra.). Both cell-based and biochemical methods are provided. In presently preferred embodiments of the assays for identification of FXR response elements, a FXR receptor, or FXR DNA binding domain is used. The ligand binding domain is preferably one for which an appropriate ligand is available. Suitable chimeric receptors are described above.

Also provided are methods of identifying response elements to which FXR does not directly bind. For example, FXR can form a transcription regulatory complex with one or more other coactivators and/or corepressors. One or more of these other molecules can actually bind to the response element. For example, FXR can bind to CPF, which in turn binds to a response element located upstream of the cyp7a gene.

In some embodiments, standard gel shift assays are performed to identify polynucleotides that can bind to a FXR DNA binding domain. These assays are performed by incubating a polypeptide that includes a FXR DNA binding domain, either as a purified protein or a complex mixture of proteins) with a labeled DNA fragment that contains the putative FXR binding site. Reaction products are analyzed on a nondenaturing polyacrylamide gel. To determine the specificity of the binding, one can perform competition experiments using polynucleotides that include a FXR binding site, or unrelated DNA sequences. Kits for performing gel shift assay include, for example, Gel Shift Assay Systems (Promega, Madison Wis., Part No. TB 10).

Another in vitro assay for identifying FXR response elements is the binding site selection method (see, e.g., U.S. Pat. No. 5,582,981). In this method, a library of oligonucleotides having a randomized nucleotide sequence of about 18 nucleotides flanked by two known nucleotide sequences of sufficient length to allow hybridization to PCR primers that are complementary to these regions. The oligonucleotides are end-labeled (e.g., with $\gamma$-$^{32}$P) and contacted with a FXR DNA binding domain polypeptide. A low stringency gel shift experiment is performed. PCR amplification is then carried out on those oligonucleotides to which the FXR DNA binding domain bound, as evidenced by retardation in the gel shift electrophoresis. Preferably, the selection and amplification process is repeated at least twice more using the amplified fragments.

In vivo assays for FXR response elements are also provided. The in vivo assays are particularly suitable for confirming results obtained in an in vitro assay. Cells are provided which contain a reporter construct that contains the putative response element in a position relative to a promoter at which binding of an FXR polypeptide can increase or decrease expression of an operably linked gene. The putative response element can be, for example, a member of a library of polynucleotide fragments. The chimeric receptor and the reporter constructs are introduced into a host cell. Suitable host cells are described in, for example, U.S. Pat. No. 5,071,773. The host cells that contain the reporter plasmid construct and the chimeric receptor are grown in the presence of the ligand for the ligand binding domain used in the chimeric receptor. Those cells in which expression of the reporter gene in the presence of the ligand is greater or less than the expression in the absence of the ligand contain a reporter construct that includes a putative response element for an FXR. The response elements can be isolated from these cells by, for example, plasmid recovery, PCR amplification, or other methods known to those of skill in the art. Upon isolation, the response elements can be characterized (e.g., by sequencing) and used to identify additional genes for which expression is influenced by FXRs.

E. Compositions, Kits and Integrated Systems

The invention provides compositions, kits and integrated systems for practicing the assays described herein. For example, the invention provides an assay system that includes an FXR polypeptide and a ligand for FXR. Also provided are assay systems for cell-based screening to identify FXR-modulating compounds. Such systems typically include an expression vector for a full-length or chimeric FXR polypeptide, a vector that contains an appropriate reporter gene under the control of a transcription complex that includes FXR, and a suitable host cell is provided by the present invention. Ligands that bind to the ligand binding domain of FXR can also be included in the assay compositions, as can modulators of FXR activity.

The invention also provides kits for practicing the FXR assay methods noted above. The kits can include any of the compositions noted above, and optionally further include additional components such as written instructions to practice a high-throughput method of assaying for FXR activity, or screening for an inhibitor or activator of FXR activity, one or more containers or compartments (e.g., to hold reagents, nucleic acids, or the like), and a control FXR activity modulator.

The invention also provides integrated systems for high-throughput screening of potential FXR modulators for an effect on binding of FXR to ligands for FXR. In other some systems, the modulation of expression of genes that are under the control of FXR, such as the cyp7a gene that modulates cholesterol metabolism, is tested. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate.

F. Pharmaceutical Compositions and Methods for Treating Cholesterol-related Disorders FXR-mediated disorders and conditions, such as atherosclerosis, cardiovascular disorders, lipid disorders and hypercholesterolemia, can be treated with therapeutic agent (s) identified using the methods described herein. The candidate therapeutic agent is typically prepared as a pharmaceutical composition and is administered to a subject suffering from a FXR-mediated disorder or condition. Preferably, the candidate therapeutic agents will, upon administration to the subject, cause total cholesterol levels to decrease about 10%, more preferably a decrease of about 20%, and most preferably a decrease of about 25–45%.

1. Pharmaceutical Compositions

Accordingly, the present invention provides pharmaceutical compositions comprising a pharmaceutically acceptable carrier or excipient and a candidate therapeutic agent. Pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

2. Treatment Regime Using Candidate Therapeutic Agents

The present invention also provides methods of modulating FXR activity in a cell. In this aspect, a cell is contacted with an FXR-modulating amount of a compound or composition above. An FXR-modulating amount can be readily determined using the assays described briefly above, or alternatively, using the assays in the Examples below. Candidate therapeutic agents are especially useful in the treatment of hypercholesterolemia.

In another aspect, the present invention provides methods of treating conditions modulated by FXR in a host animal, by administering to the host an effective amount of a compound or composition provided above. In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally.

A variety of conditions are modulated, at least in part, by FXR, including hypercholesterolemia or other conditions associated with abnormal cholesterol or lipid homeostasis such as atherosclerosis, lipid disorders and cardiovascular disorders. The compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

Typically, the host or subject in each of these methods is human, although other animals can also benefit from the foregoing treatments.

EXAMPLES

The following examples are offered to illustrate, but not to limit the present invention. Some of these experiments are described in Makishima et al. (1999) *Science* 284: 1362–1365, which was published after the priority date of the instant application.

EXAMPLE I
CDCA Specifically Transactivates FXR

This Example demonstrates that the primary bile acid chenodeoxycholic acid (CDCA) specifically activates the gene expression regulatory activity of FXR. The experiment was conducted using fusion polypeptides in which a ligand binding domain of FXR and other nuclear receptors were independently linked to the DNA binding domain (DBD) of Gal4. These in-frame fusions of the Gal4 DNA-binding domain (Gal4 DBD, pM3 expression vector) and the ligand-binding domains (LBDs) of FXR, HNF4α, LXRα, RXRα and LXRβ nuclear receptors were used to determine the specificity of FXR transactivation by chenodeoxycholic acid (CDCA).

HepG2 cells were transiently transfected with a reporter plasmid in which a luciferase-encoding gene was under the control of a pGL3 5X GAL4 response element (which consists of five GAL4 binding elements) (0.25 $\mu$g/1.5×10$^5$ cells). The cells were also transfected with the empty expression vector pM3 or the pM3-LBD fusion expression plasmids (0.25 $\mu$g/1.5×10$^5$ cells) as indicated. Luciferase reporter activity was measured after treating cells with or without 50 $\mu$M CDCA. For each fusion plasmid, fold activation is a ratio of luciferase activity (normalized by β-galactosidase activity) between treated and untreated cells. The FXR fusion construct was the sole receptor transactivated by CDCA (see, FIG. 1A).

Figure 1B:
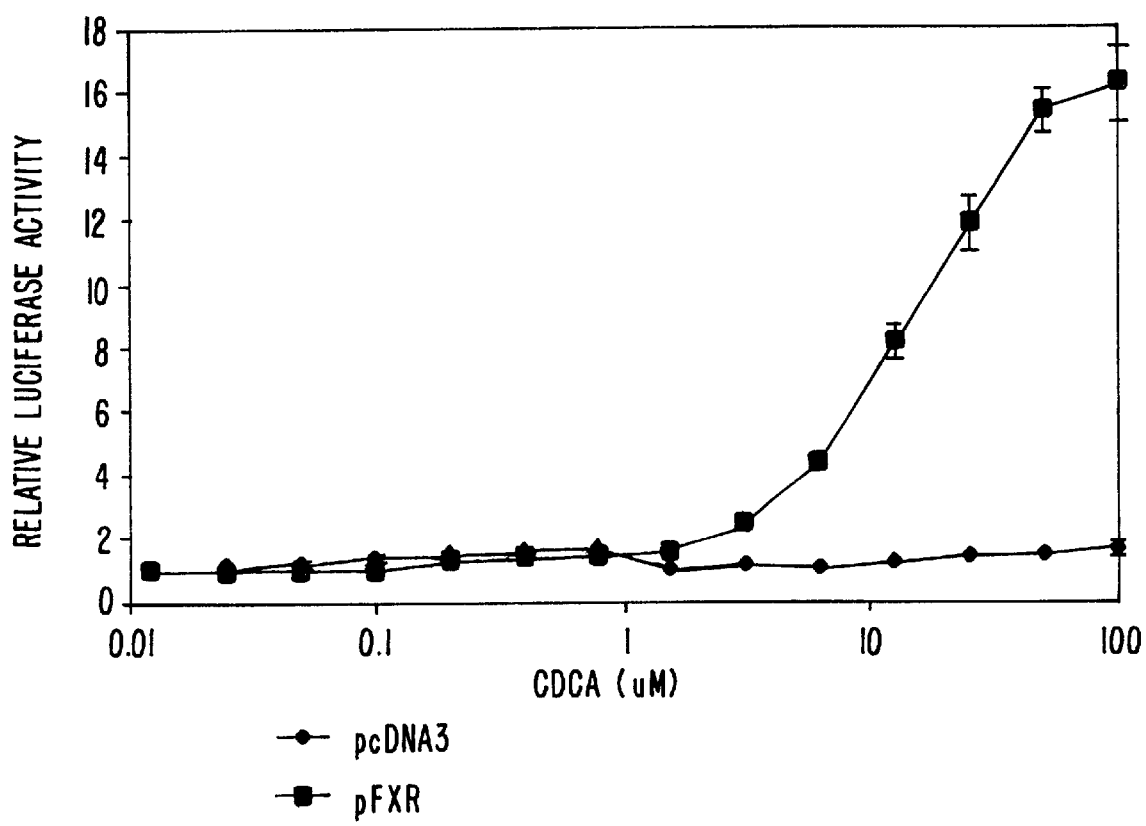

This example further illustrates that CDCA-mediated transactivation of FXR is dose-dependent. HepG2 cells were transiently transfected with the pGL3 3X FXRE (three FXR response elements, AGGTCAATGACCT; SEQ ID NO:1) luciferase reporter plasmid (0.25 $\mu$g/1.5×10$^5$ cells), plus empty expression vector (pcDNA3) or a plasmid expressing full-length FXR (PFXR) (0.15 $\mu$g/1.5×10$^5$ cells). Luciferase reporter activity was measured after treating cells with or without CDCA (concentrations as indicated). Fold activation was calculated as the ratio of luciferase activity (normalized by β-galactosidase activity) between treated and untreated cells. A dose-dependent transactivation (IC$_{50}$ 10 $\mu$M CDCA) of the reporter gene by FXR was observed (see, FIG. 1B).

EXAMPLE II
FXR Suppresses CYP7 Expression

Figure 2A:
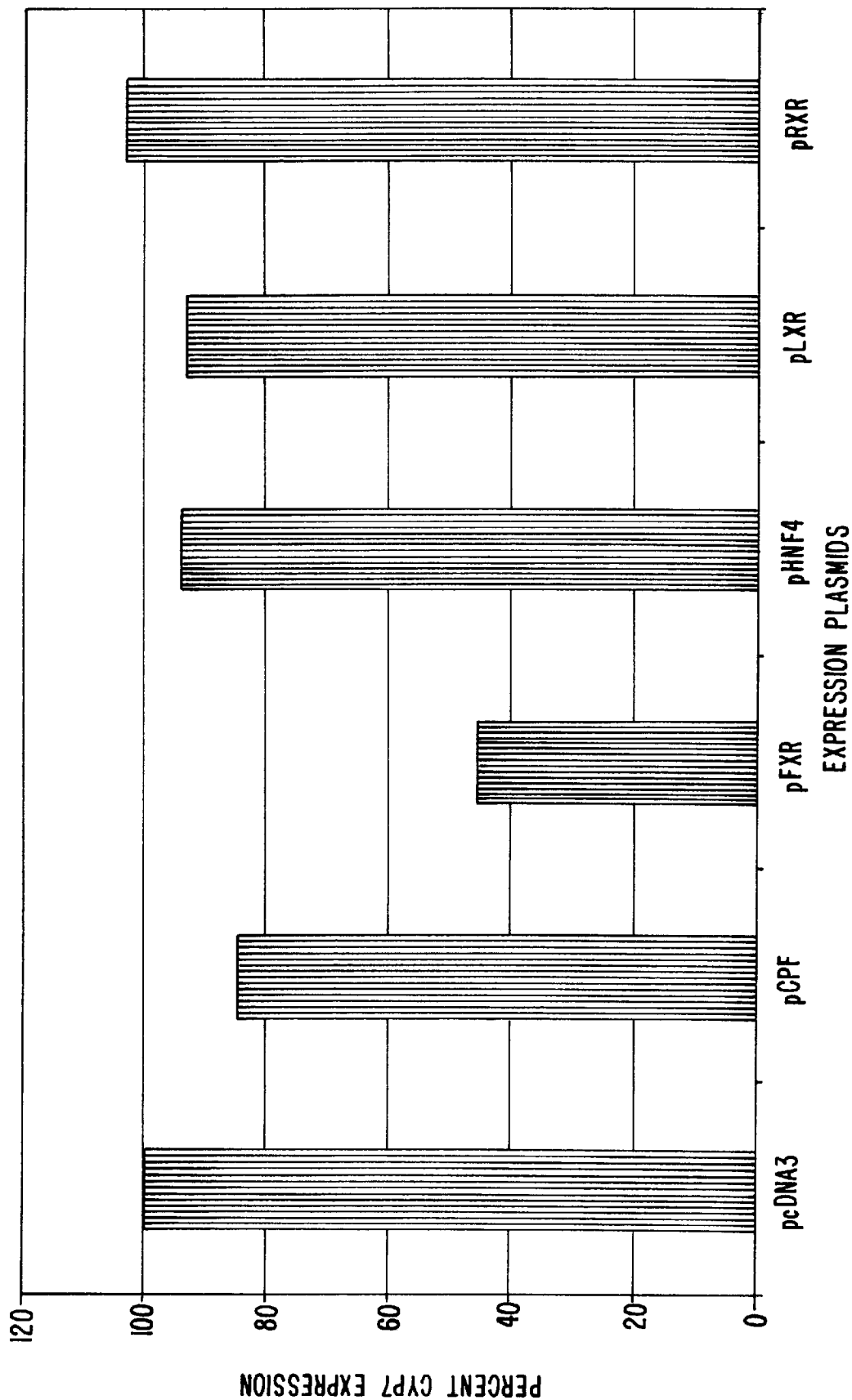
FIGS. 2A and 2B illustrate that FXR suppresses cyp7 expression.

This example illustrates that CDCA-mediates FXR-specific suppression of CYP7 expression. Full-length nuclear receptors FXR, CPF, HNF4α, LXRα and RXRα were assayed to determine their ability to suppress CYP7 expression in the presence of 10 $\mu$M CDCA. In this experiment, a luciferase reporter plasmid under the control of the cyp7a promoter (−718 to +14, where +1 designates the transcriptional start site) (pGL3-CYP7) was used. HepG2 cells were transiently transfected with the pGL3-CYP7 luciferase reporter (0.25 $\mu$g/1.5×10$^5$ cells) plus empty expression vector (pcDNA3) or plasmids expressing one of the indicated nuclear receptors (0.25 $\mu$g/1.5×10$^5$ cells). Luciferase reporter activity was measured after treating cells with or without 10 pM CDCA. The ratio of luciferase activity (normalized by β-galactosidase activity) between treated and untreated pcDNA3-transfected cells was set at 100 percent CYP7 expression. The percent CYP7 expression for the nuclear receptors was normalized to that of pcDNA3. Only FXR suppressed CYP7 expression under these conditions (see, FIG. 2A).

Figure 2B:
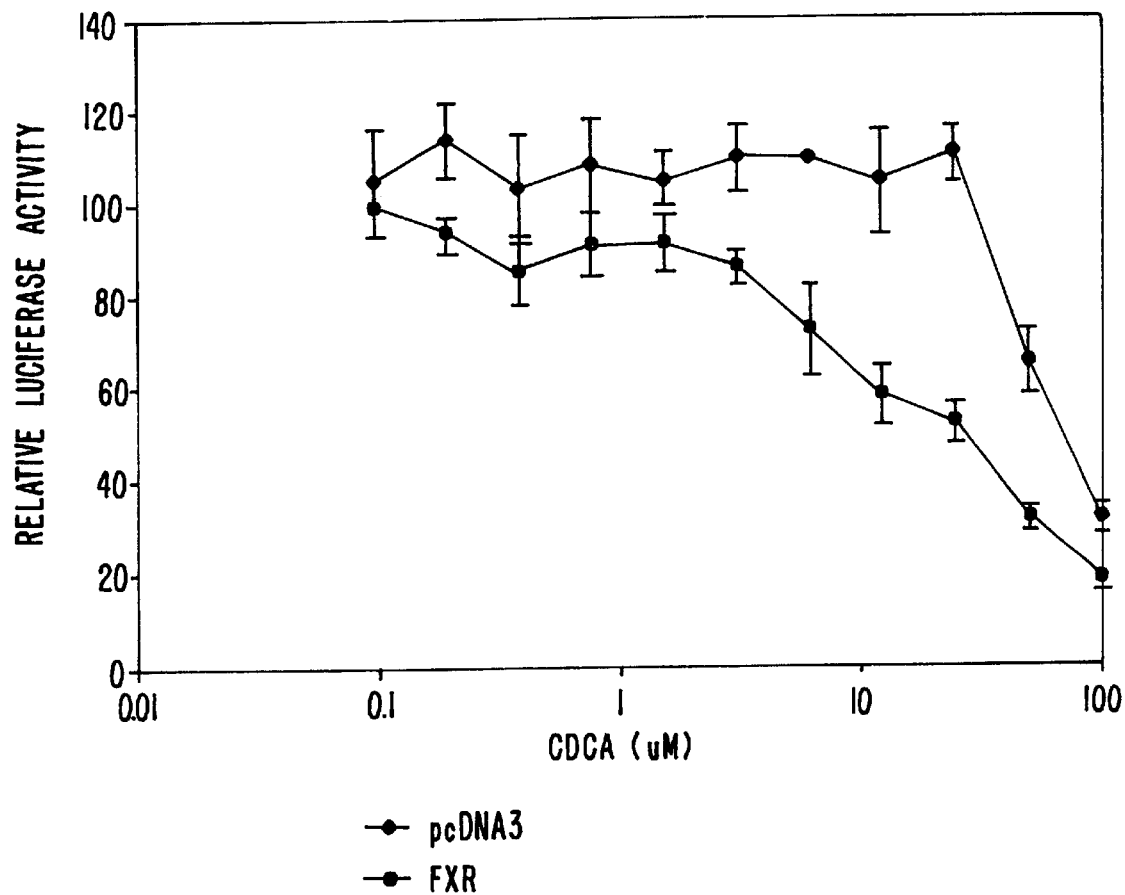

This example further illustrates the dose response profile of CDCA-mediated suppression of CYP7 expression by FXR. HepG2 cells were transiently transfected with the pGL3-CYP7 luciferase reporter plasmid (0.25 $\mu$g/1.5×10$^5$ cells), plus empty expression vector (pcDNA3) or a plasmid expressing full-length FXR (PFXR) (0.15 $\mu$g/1.5×10$^5$ cells). Luciferase reporter activity was measured after treating cells with or without CDCA (concentrations as indicated). The presence of FXR alone suppresses CYP7 expression, and this suppression is enhanced with the addition of CDCA (see, FIG. 2B).

EXAMPLE III
FXR Suppression Specific to CYP7

Figure 3A:
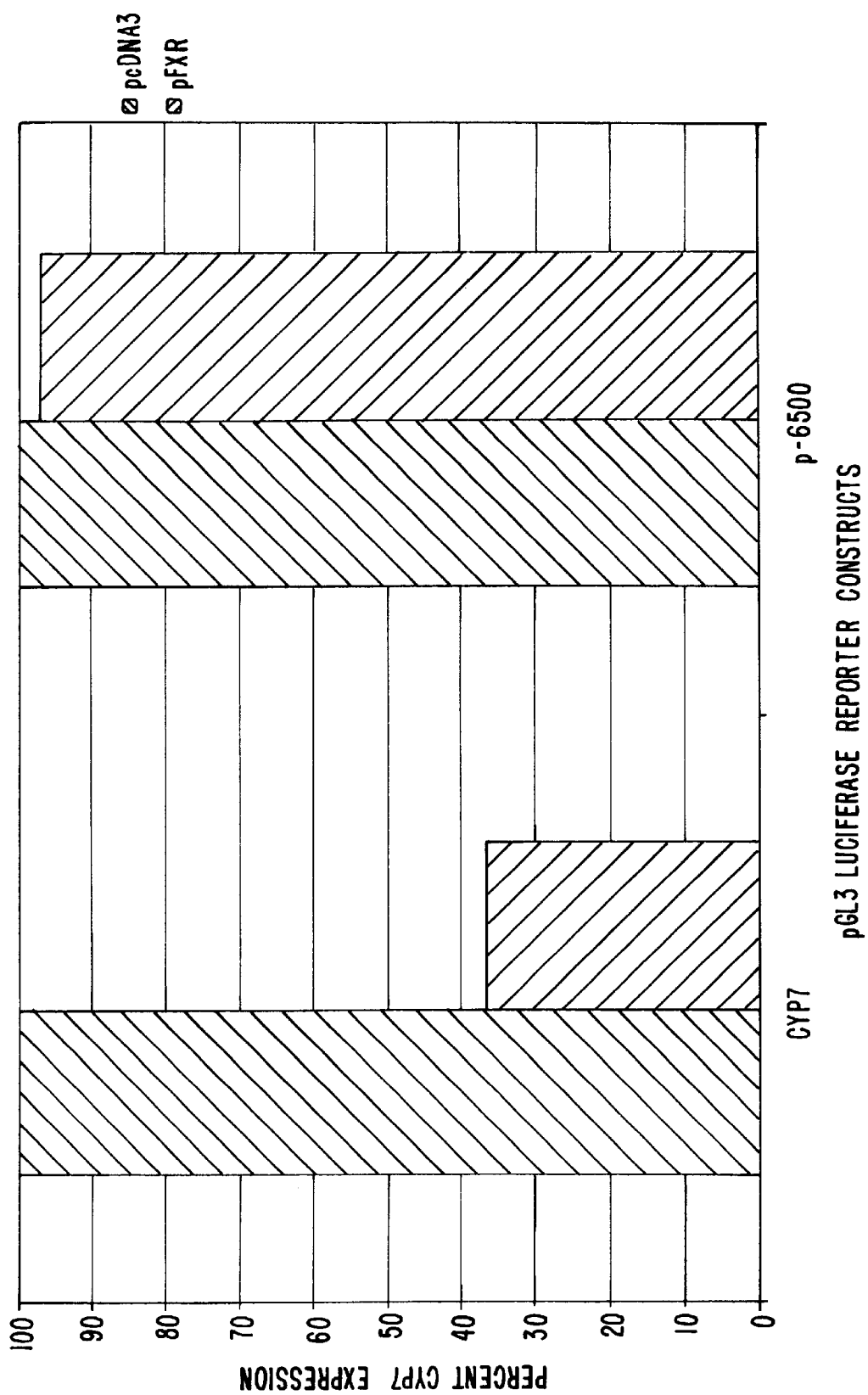
FIGS. 3A, 3B and 3C illustrate that FXR suppression is specific to cyp7.

This example illustrates that CDCA-mediated FXR suppression is specific for CYP7. FXR does not suppress expression of the low density lipoprotein (LDL) receptor. This experiment was conducted using a second luciferase reporter plasmid, named p-6500, in which the luciferase gene is under the control of a 6.5 kilobase pair (kb) promoter region of the LDL receptor. HepG2 cells were transiently transfected with pGL3-CYP7 or p-6500. Cells were also transfected with either empty expression vector (pcDNA3) or a plasmid that expresses full-length FXR (PFXR) (all at 0.25 $\mu$g/1.5×10$^5$ cells). Luciferase reporter activity was measured after treating cells with or without 10 $\mu$M CDCA. The ratio of luciferase activity (normalized by $\beta$-gatactosidase activity) between treated and untreated pcDNA3-transfected cells was set at 100 percent CYP7 expression. No FXR/CDCA-mediated suppression of the p-6500 reporter was observed (see, FIG. 3A).

Figure 3B:
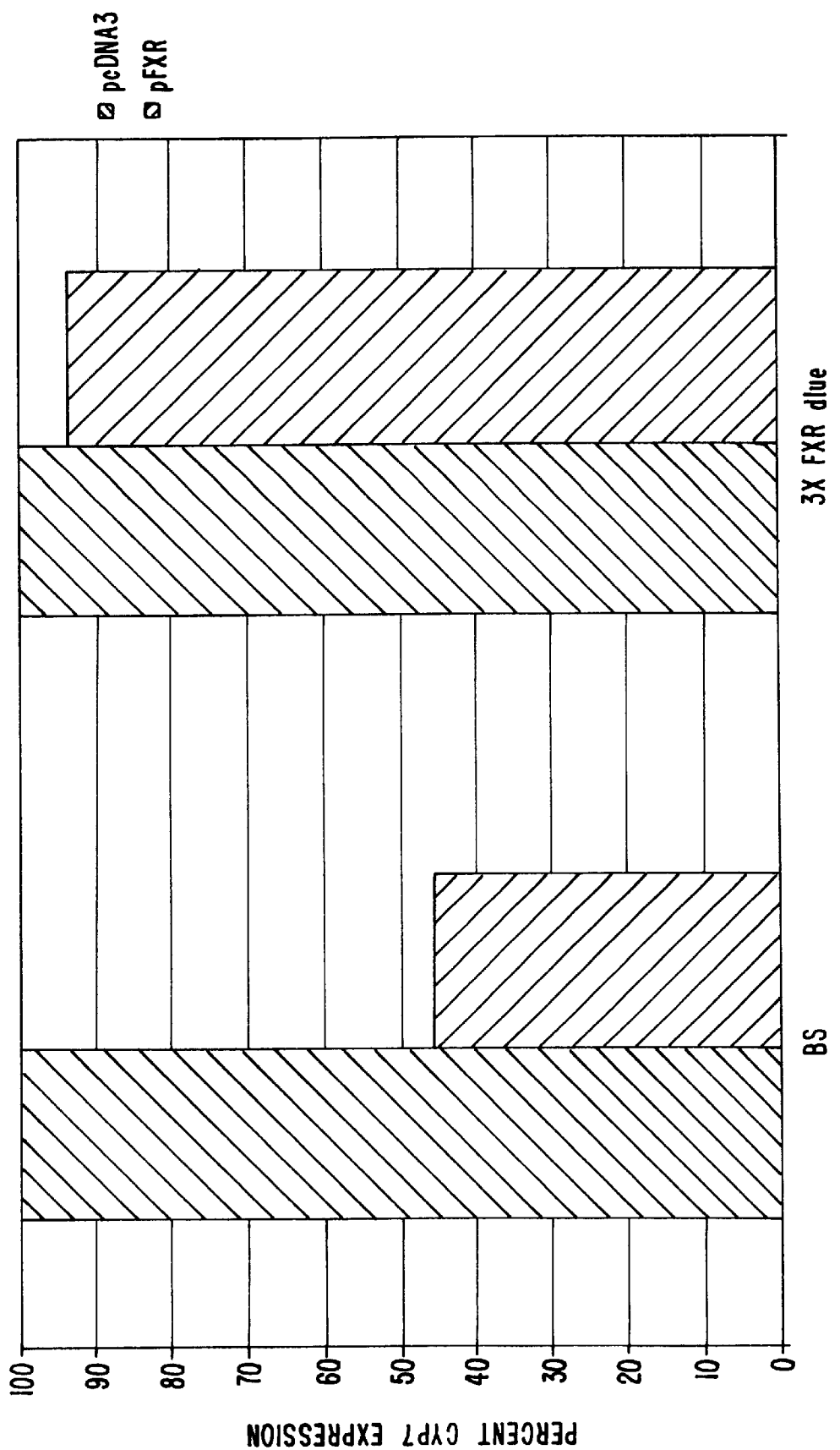

This example further illustrates that CYP7 suppression is lost upon titrating away FXR. HepG2 cells were transiently transfected with pGL3-CYP7 luciferase reporter plasmid (50 $\mu$g/1.5×10$^5$ cells), plus an empty expression vector (pcDNA3) or a plasmid expressing full-length FXR (pFXR) (0.25 $\mu$g/1.5×10$^5$ cells). Cells were also transfected with a competitor plasmid, either pBSKS or pGL3 3X FXRE $\Delta$luc (0.5 $\mu$g/1.5×10$^5$ cells). Luciferase reporter activity was measured after treating cells with or without 10 $\mu$M CDCA. For each competitor, the ratio of luciferase activity (normalized by $\beta$-galactosidase activity) between treated and untreated pcDNA3-transfected cells was set at 100 percent CYP7 expression. Loss of CYP7 suppression was-observed when ten-fold excess pGL3 3X FXR $\Delta$luc was cotransfected with the CYP7 reporter gene (see, FIG. 3B). This result strongly suggests that FXR is a component of the bile acid-mediated suppression of CYP7.

Figure 3C:
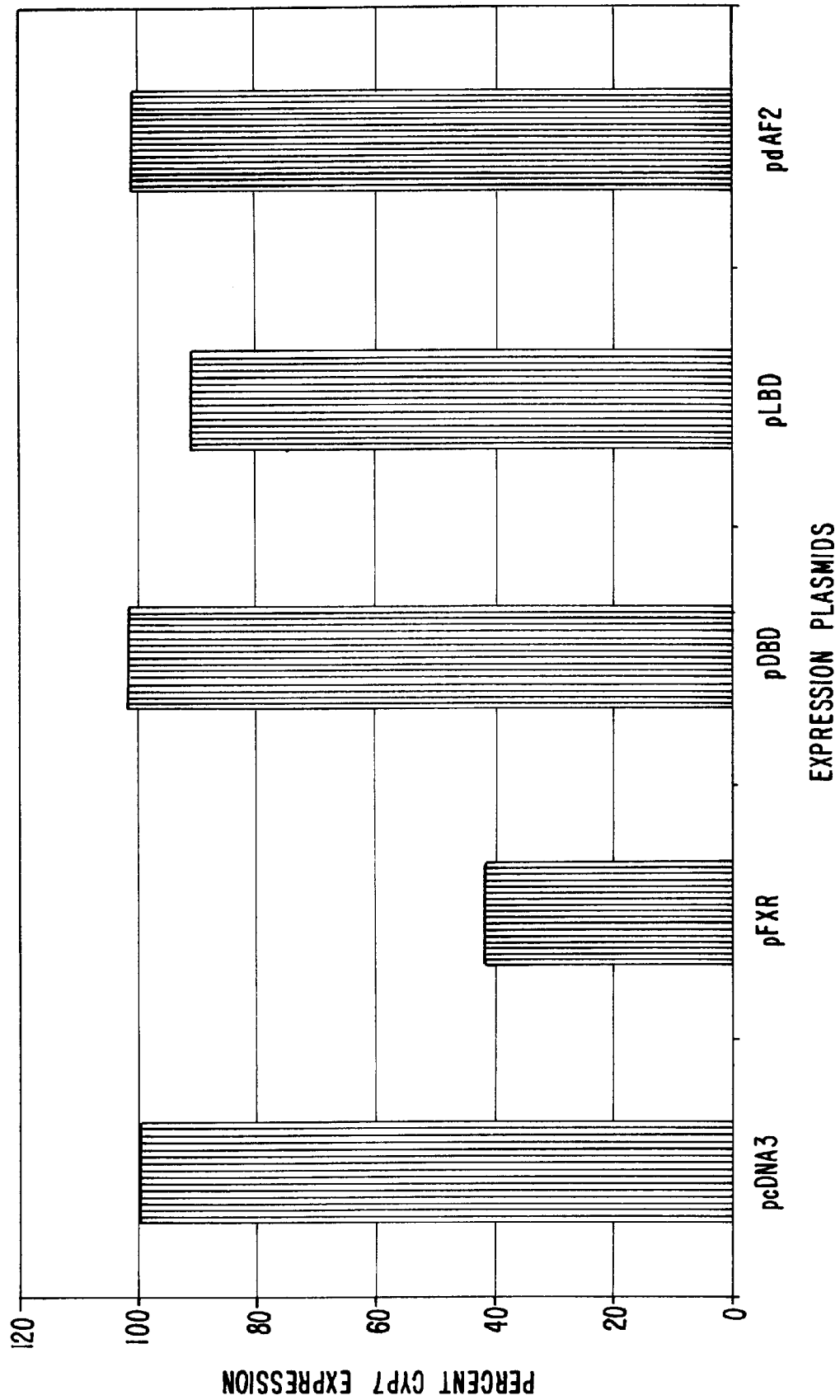

This example further illustrates that FXR mutants do not suppress CYP7 expression. FXR mutants were created and assayed to determine whether they are able to suppress CYP7 in a CDCA-dependent manner. HepG2 cells were transiently transfected with the pGL3-CYP7 luciferase reporter plasmid (0.25 $\mu$g/1.5×10$^5$ cells), plus empty expression vector (pcDNA3) or a plasmid expressing full-length wild-type FXR (pFXR) or mutant (DNA-binding domain [DBD], ligand-binding domain [pLBD], and AF2 domain truncation [dAF2]) FXR (0.25 $\mu$g/1.5×10$^5$ cells). Luciferase reporter activity was measured after treating cells with or without 10 $\mu$M CDCA. The ratio of luciferase activity (normalized by $\beta$-galactosidase activity) between treated and untreated pcDNA3-transfected cells was set at 100 percent CYP7 expression. None of the FXR derivatives had any effect upon CYP7 suppression (see, FIG. 3C).

EXAMPLE IV

Bile Acids and FXR Repress Cyp7A Promoter

This example demonstrates that bile acids and FXR repress expression from the promoter for the cholesterol 7$\alpha$-hydroxylase (Cyp7A) gene, which is the rate-limiting enzyme in cholesterol metabolism. Both the expression of Cyp7A protein and MRNA (FIG. 4A in a hepatocyte-derived cell line were analyzed. HepG2 cells were seeded at an initial density of 1×10$^6$ cells/well in a 6-well plate, and allowed to grow for approximately 24 hours at 37° C., 5% $CO_2$ in DMEM-F12 medium (Mediatech) supplemented with 10% fetal calf serum. Once the cell culture became confluent, the medium was replaced with DMEM-F 12 without serum, and supplemented with primary or conjugated bile acids at a final concentration of 50 $\mu$M. The cultures were then incubated at 37° C., 5% $CO_2$ for 24 hours.

An immunoblot analysis using an antibody to Cyp7a was performed on lysates from human HepG2 cells after treatment with bile acids. Quantitative RT-PCR analysis of CYP7A MRNA in HepG2 cells was performed as follows. Total RNA was prepared from HepG2 cells using Tri Reagent (Molecular Research Center, Inc.), according to the recommendations of the manufacturer. Following extraction with Tri Reagent and precipitation with ethanol, the RNA was resuspended in DEPC-treated water and stored at −80° C. prior to analysis. The following primers were used for amplification and analysis of human CYP7 mRNA by RT-PCR: CYP7$_{-78}$: 5'-tgatttgggggattgctata-3' (SEQ ID NO:2), CYP7$_{-178}$: 5'-catacctgggctgtgctct-3' (SEQ ID NO:3), and CYP7$_{-132}$(FAM): 5'-(6-FAM)tggttcacccgtttgccttctcct (TAMRA)-3' (SEQ ID NO:4). As a control, a primer set for detection of human GAPDH mRNA was used; this set is commercially available and was obtained from Applied Biosystems/Perkin Elmer, Inc.

Amplification of specific target mRNAs was carried out by reverse transcription followed by polymerase chain reaction using the TaqMan One Step Gold RT-PCR Kit (Applied Biosystems/Perkin Elmer, Inc.). Each primer set included a pair of amplification primers and the fluorogenic probe primer as indicated, and were present in the reaction at a final concentration of 100 nM/ primer. One $\mu$g of total RNA isolated from the various culture conditions was used as template in individual RT-PCR reactions.

Analysis of GAPDH MRNA and CYP7A MRNA were carried out in triplicate in parallel reactions. Reactions were carried out using the ABI Prism 7700 Sequence Detector (Perkin Elmer, Inc.) Reverse transcription was allowed to proceed for 30 minutes at 48° C., followed by amplification of the cDNA by 40 cycles of PCR, each consisting of a melting step (95° C. for 15 seconds) and a combined annealing-extension step (60° C. for 1 minute). During PCR, the cycle-to-cycle changes in fluorescence due to template amplification were monitored, allowing the amount of amplified product to be determined, and the initial template concentration to be calculated. These values were used to compare the steady-state levels of accumulated CYP7A and GAPDH MRNA in HepG2 cells grown in the presence and absence of bile acids (see, FIG. 4A).

Figure 4A:
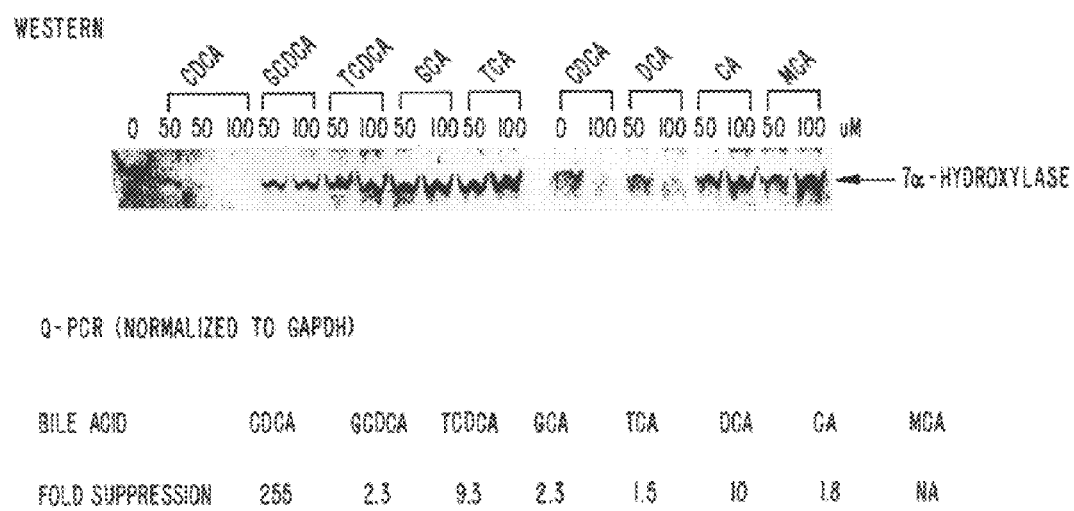
FIGS. 4A and 4B, 4C and 4D illustrate the effect of different bile acids on FXR activity.
Figure 4B:
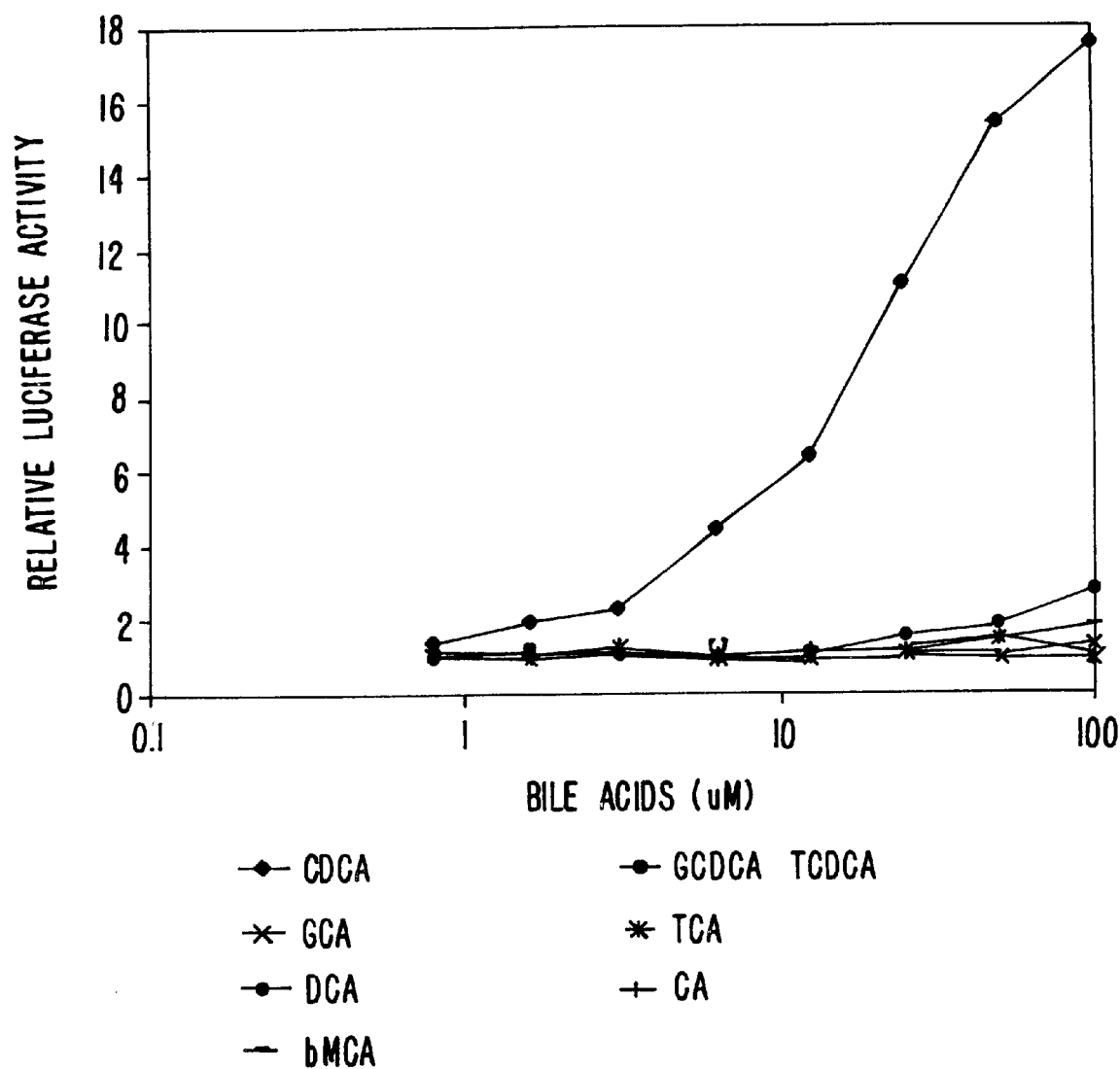

Also examined was the effect of bile acids on coactivator recruitment to FXR. A mammalian two-hybrid assay was used to demonstrate that FXR interacts with the coactivator SRC-1. In this experiment, a plasmid expressing a GAL4 DNA-binding domain-SRC-1 fusion protein and a plasmid expressing an FXR ligand-binding domain-VP-16 fusion protein were used. HepG2 cells were transiently transfected with the pG5 luciferase reporter plasmid (a luciferase gene under the control of five GAL4 binding sites) (0.25 $\mu$g/1.5× 10$^5$ cells) and the plasmids expressing the two fusion proteins. Luciferase reporter activity was measured after treating cells with or without the panel of bile acids (concentrations as indicated) (FIG. 4B). Relative luciferase activity is a ratio of luciferase activity (normalized by $\beta$-galactosidase activity) between treated and untreated cells.

Figure 4C:
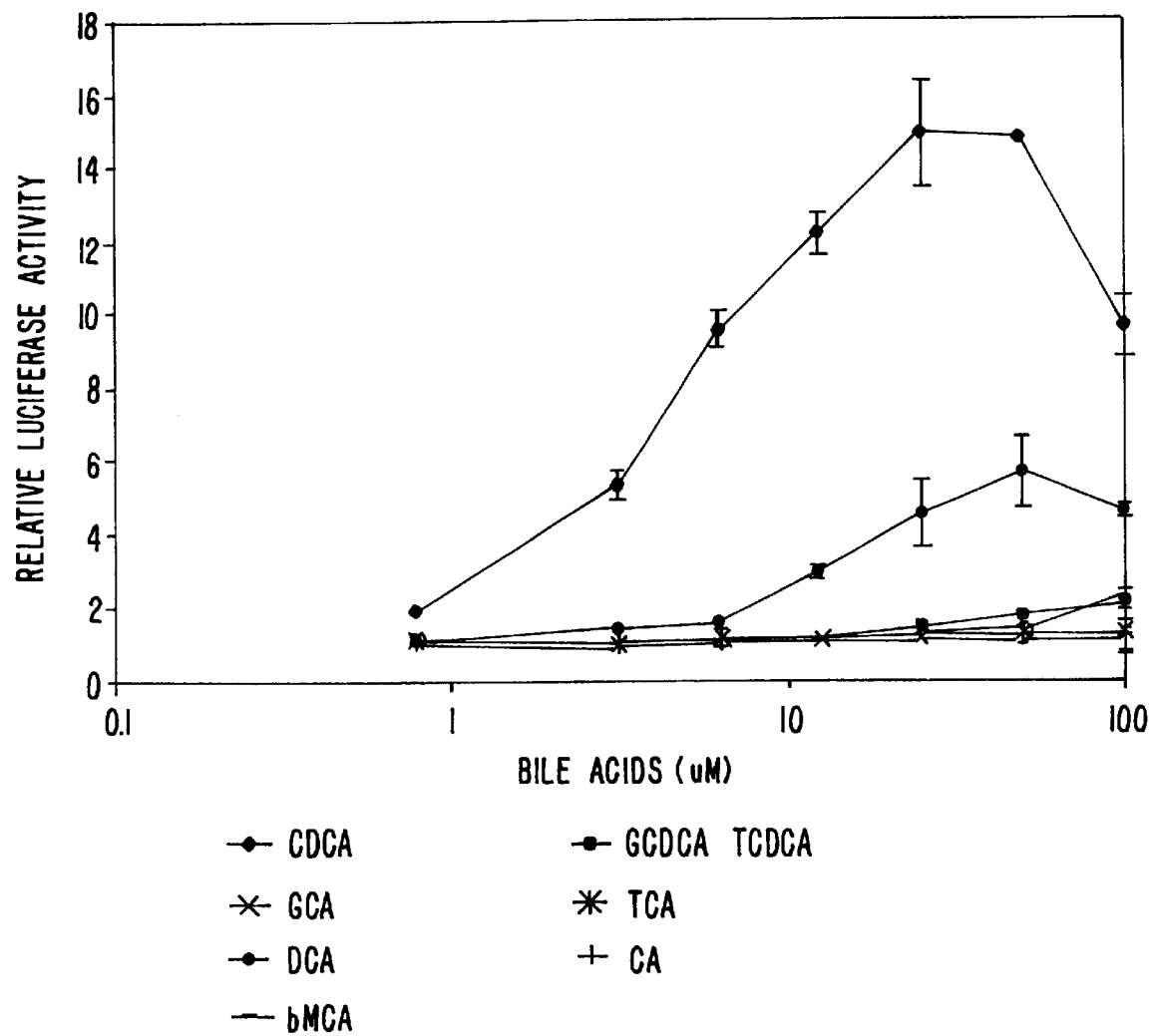

The ability of different bile acids and derivatives to activate FXR-mediated transactivation was also examined. HepG2 cells were transiently transfected with the pGL3 3X FXRE luciferase reporter plasmid (0.25 $\mu$g/1.5×10$^5$ cells) and a plasmid expressing full-length FXR (pFXR) (0.15 $\mu$g/1.5×10$^5$ cells). Luciferase reporter activity was measured after treating cells with or without the panel of bile acids (concentrations as indicated). Fold activation is a ratio of luciferase activity (normalized by $\beta$-galactosidase activity) of treated and untreated cells. Treatment with CDCA, followed by deoxycholic acid (DCA) and glycochenodeoxycholic acid (GCDCA), had the greatest induction of luciferase reporter activity (FIG. 4C).

The effect of different bile acids and derivatives on FXR-mediated suppression of CYP7 expression was also studied. HepG2 cells were transiently transfected with the pGL3-CYP7 luciferase reporter plasmid (0.25 µg/1.5×10$^5$ cells) and a plasmid expressing full-length FXR (PFXR) (0.15 µg/1.5×10$^5$ cells). Luciferase reporter activity was measured after treating cells with or without the panel of bile acids (concentrations as indicated). Luciferase reporter activity for untreated cells was defined as 100% percent CYP7 expression. The highest level of suppression of CYP7 expression was observed with CDCA treatment followed by DCA (see, FIG. 4D).

Figure 4D:
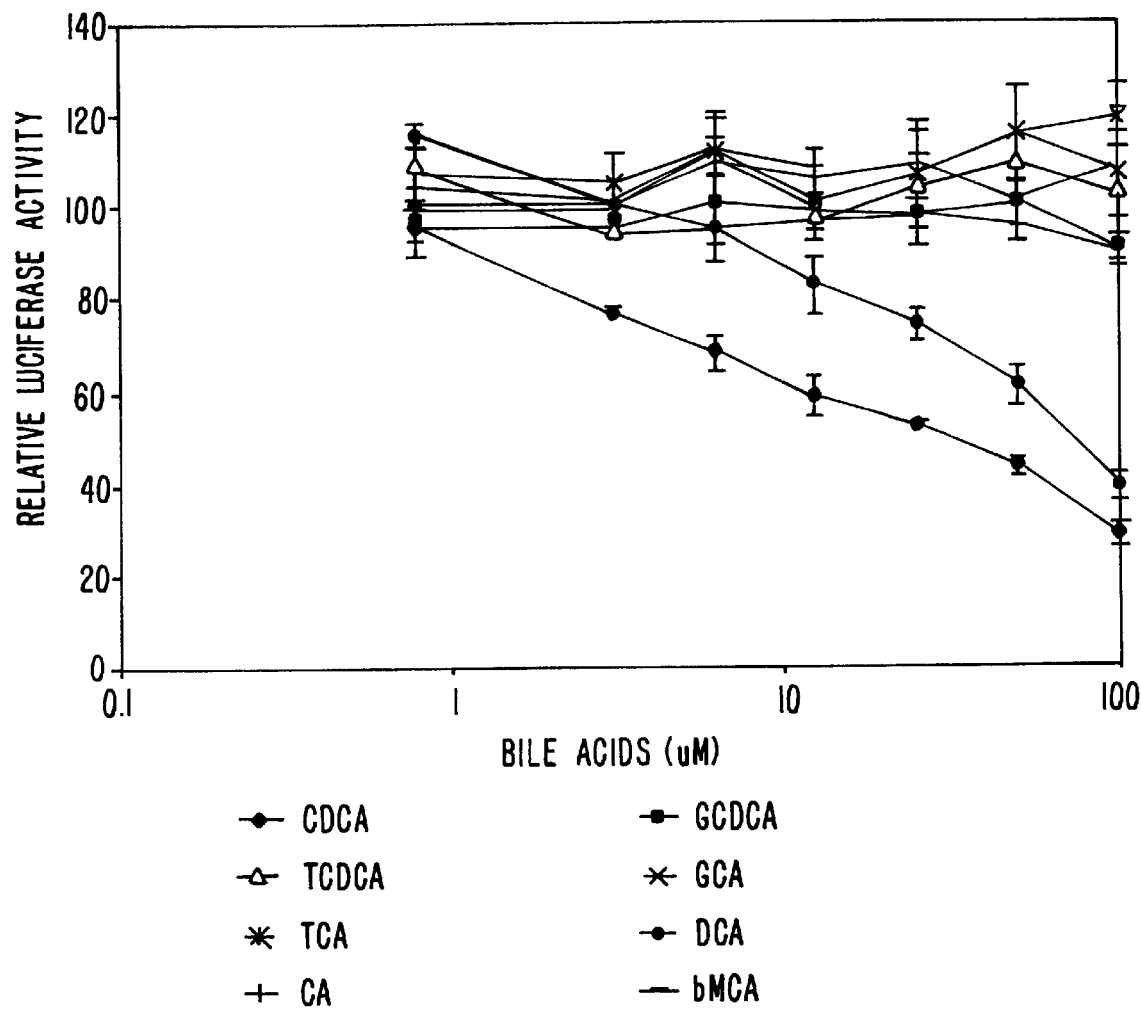

CDCA treatment resulted in the largest induction of luciferase activity (see, FIGS. 4B and 4C), and also the largest repression of CYP7a expression (FIG. 4D). The rank order of bile acids in these activity-measuring experiments was the same as that for repressing endogenous expression of human Cyp7a protein and mRNA (FIG. 4A)

EXAMPLE V

High-Throughput In Vitro Biochemical Assays

This Example describes three different high throughput in vitro assay that are useful for screening to identify compounds that can modulate binding of FXR ligands to the FXR ligand binding domain. The ability of different bile acids and derivatives to affect the binding of a labeled sensor peptide that is derived from the coactivator SRC-1 to an FXR ligand binding domain was tested.

Fluorescence Polarization

Fluorescence polarization was used to study the effect of different bile acids on the ability of the FXR LBD to bind a sensor peptide. The assay reagents were as follows:

Reagents:
  Sensor: Rhodamine-labeled ILRKLLQE (SEQ ID NO:5) peptide (final conc.=1–5 nM). It is noted that the Rhodamine-labeled peptide comprises, at a minimum, the following sequence LXXLLXX, wherein X is any amino acid. Additional amino acids can be added to both the N-terminus and the C-terminus of this core peptide. In preferred embodiments, the peptide is 8 amino acids in length and, more preferable, about 11 amino acids in length.
  Receptor: Glutathione-S-transferase/FXR ligand binding domain fusion protein (fmal conc.=100–200 nM).
  Buffer: 10 mM HEPES, 10 mM NaCl, 6 mM magnesium chloride, pH 7.6

Protocol:
1. Add 90 microliters of Sensor/Receptor mixture to each well of a 96-well microtiter plate.
2. Add 10 microliters of test compound per well.
3. Shake 5 minutes and within 5 minutes determine the amount of fluorescence polarization by using a Fluorolite FPM-2 Fluorescence Polarization Microtiter System (Dynatech Laboratories, Inc.

Figure 5A:
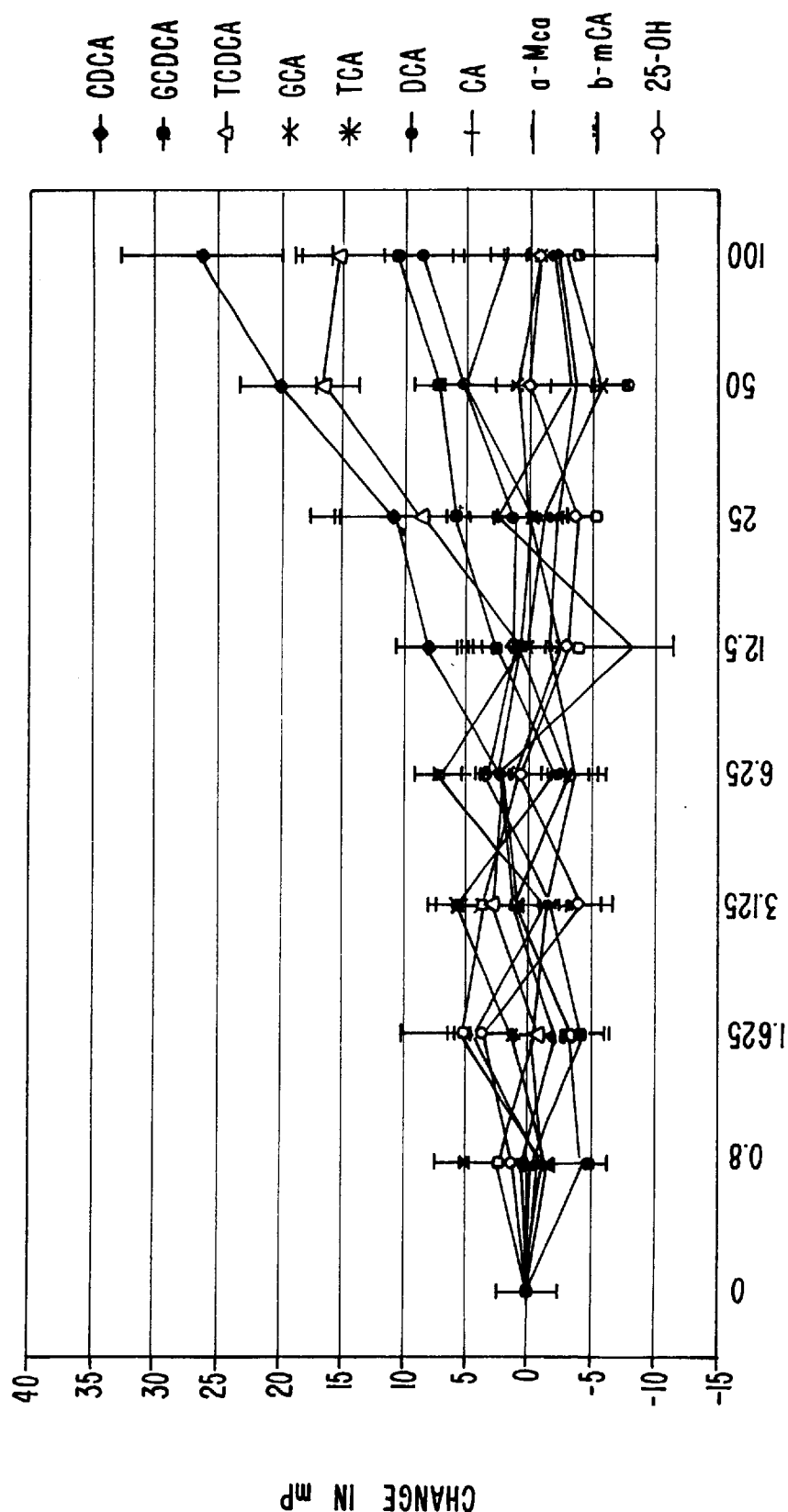
FIG. 5A illustrates the results of a peptide sensor assay using a GST-FXR fusion protein. The binding of the peptide sensor to the FXR LBD in the presence of different bile acids and derivatives was analyzed by fluorescence polarization.

Ten ng/µL of GST-FXR fusion protein was mixed with a rhodamine-labeled peptide comprising LXXLLXX, wherein X is any amino acid, and the panel of bile acids (concentrations as indicated). Fluorescence polarization was read after a room temperature incubation and brief shaking. Change in millipolarization (mP) units is the difference treated and untreated samples. The high change in mP units demonstrates that the labeled peptide binds to GST-FXR in a CDCA-dependent manner (see, FIG. 5A).

Fluorescence Resonance Energy Transfer

Figure 5B:
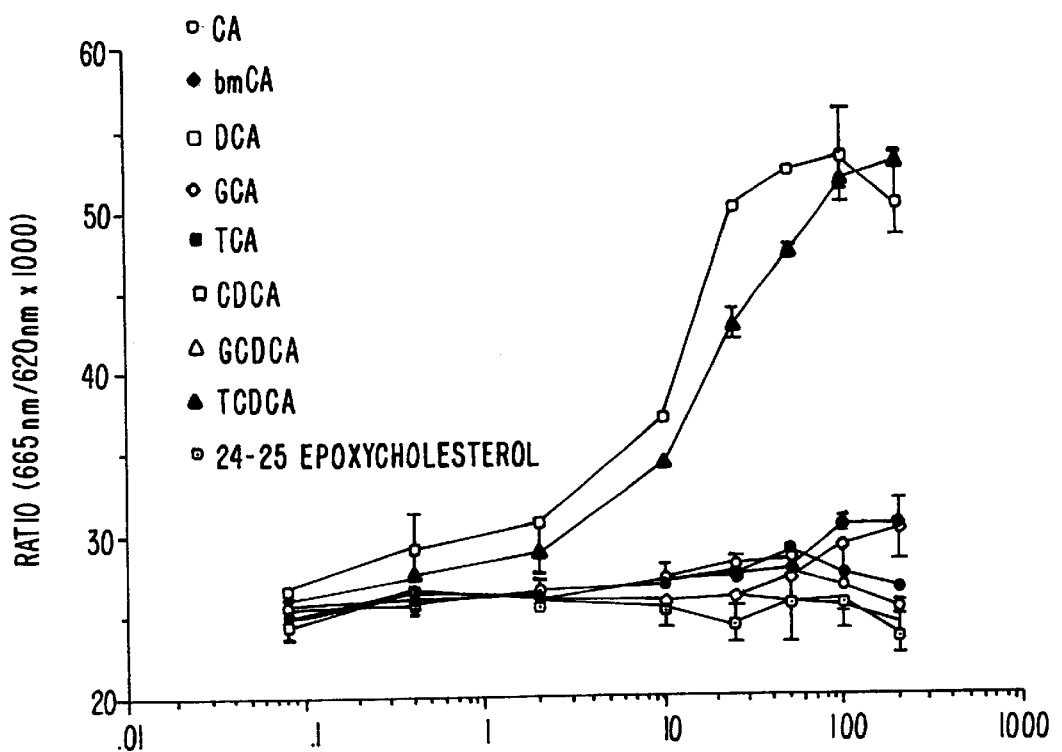
FIG. 5B shows the results of an analysis in which FRET was used to monitor the effect of bile acids and derivatives on FXR/SRC-1 interaction.
Figure 5B:
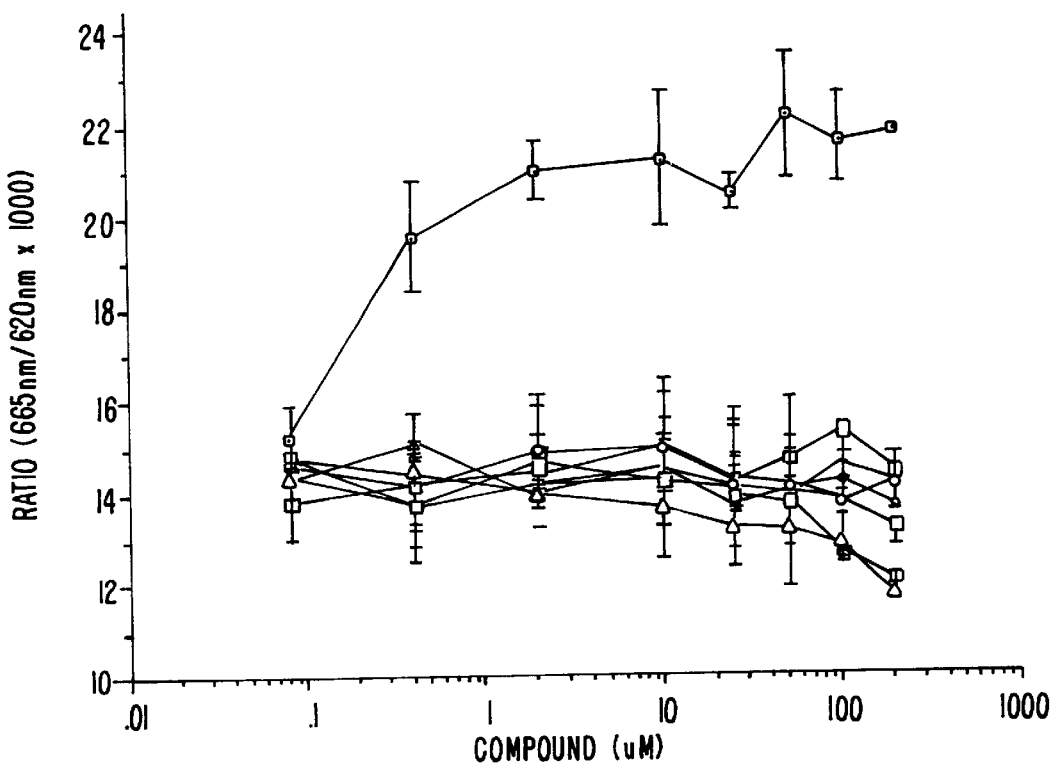

FIG. 5B shows the results of an experiment in which fluorescence resonance energy transfer (FRET; also referred to as HTRF) was used to study the effect of different bile acids on the ability of FXR to bind the coactivator SRC-1. The top panel shows that FXR-SRC-1 binding is stimulated by bile acids. The bottom panel of FIG. 5B shows that the binding of the LXRα receptor control is affected not by the bile acids, but rather by the LXRα ligand 24,25 epoxycholesterol.

ELISA

Figure 5C:
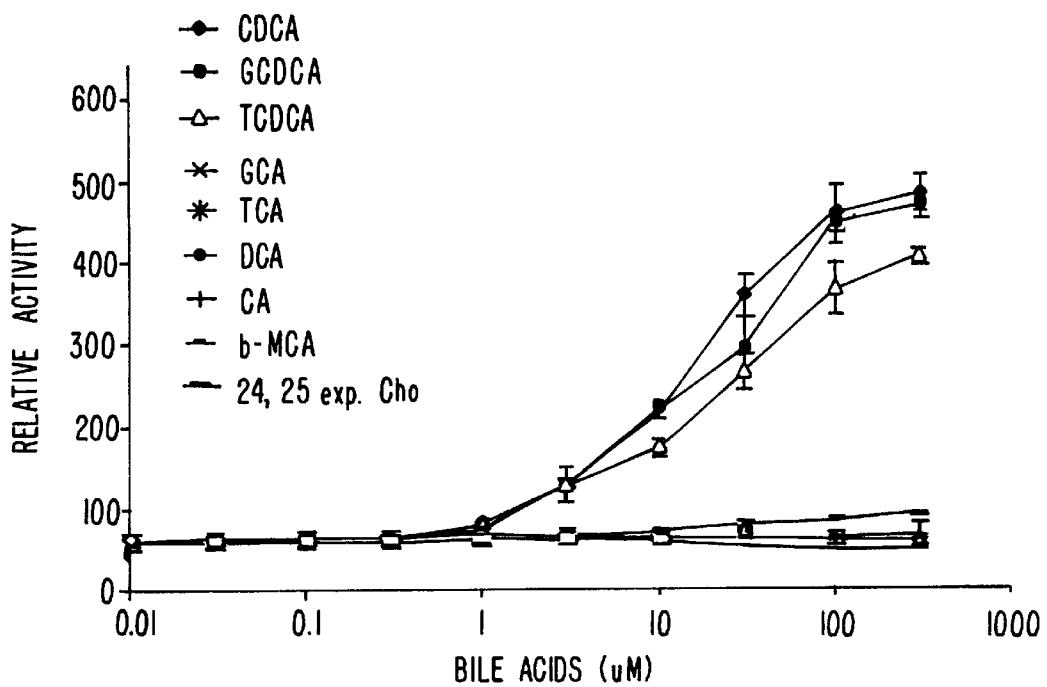
FIG. 5C shows the results of a sensor peptide study in which ELISA was used to detect binding of the sensor peptide to the FXR LBD in the presence of increasing concentrations of different bile acids and derivatives.
Figure 5C:
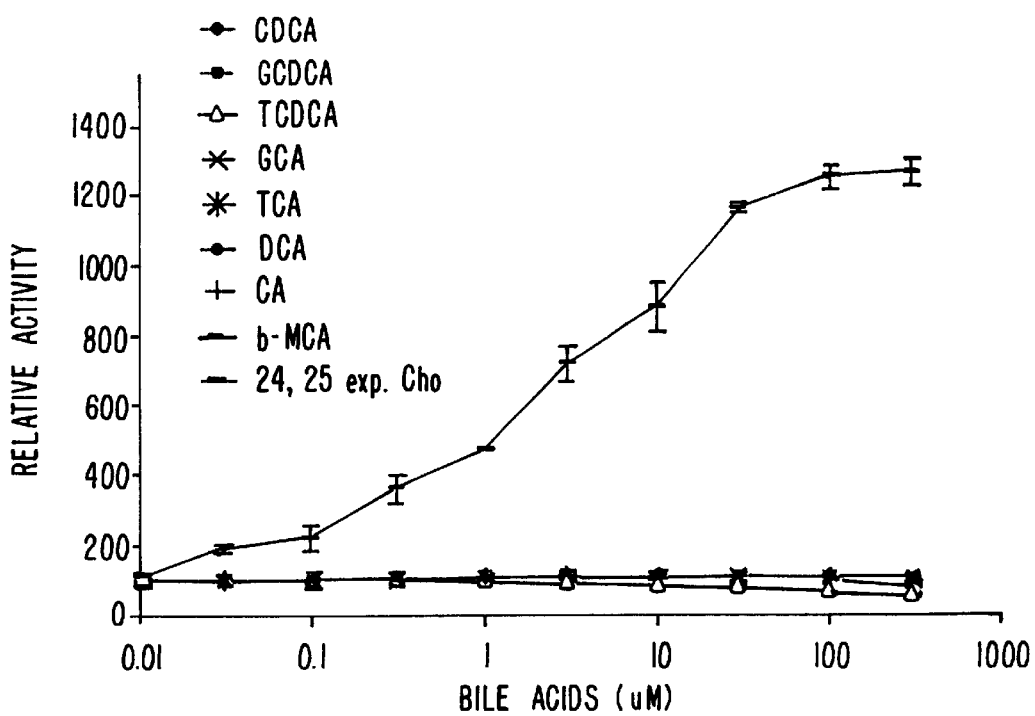

An enzyme-linked immunosorbent assay (ELISA) was used to study the effect of bile acids on ligand-induced conformational changes of FXR. A peptide sensor was used. The results, which are shown in FIG. 5C, demonstrate that increasing concentrations of bile acids (in particular, CDCA) result in an increase in the amount of peptide sensor that is bound to the FXR ligand binding domain. The binding of the sensor peptide to the LXRα control (bottom panel), in contrast, was not affected by the bile acids. Only the LXRα ligand 24,25 epoxycholesterol resulted in increased binding of the sensor peptide to LXRα.

From the foregoing examples, it is readily apparent that the orphan nuclear receptor FXR is involved in the bile acid-dependent suppression of the human cyp7 gene. The primary bile acid CDCA (chenodeoxycholic acid) specifically transactivates FXR and does so in a dose-dependent manner ($IC_{50}$=10 M). Overexpression of FXR was found to suppress cyp7 expression and the suppression was enhanced in the presence of CDCA. This enhanced suppression is specifically mediated by FXR and seems to be specific to the cyp7 promoter. By using a panel of bile acids, it was demonstrated that the bile acid-mediated FXR activation correlates with bile acid-mediated human cyp7 suppression. Moreover, by using an in vitro biochemical peptide sensor assay and the cell-based mammalian two-hybrid assay, it was demonstrated that when FXR is bound by CDCA, the activated complex is able to recruit SRC-1 to the complex. In summary, the results strongly suggest that FXR functions as a bile acid receptor/sensor that mediates-cyp7 expression in a bile-acid dependent manner.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of prescreening to identify a candidate therapeutic compound suitable for testing for ability to modulate cholesterol metabolism in a cell, said method comprising:
   providing a reaction mixture that comprises:
   a) a polypeptide that comprises a ligand binding domain of an FXR;
   b) a ligand for FXR; and
   c) a test compound; and
   determining whether the amount of binding of the FXR ligand binding domain to the ligand for FXR is increased or decreased in the presence of the test compound compared to the amount of binding in the absence oft he test compound;
   wherein a test compound that causes an increase or decrease in binding is a candidate therapeutic agent for modulation of cholesterol metabolism.

2. The method of claim 1, wherein the method further comprises administering the candidate therapeutic agent to a cell to determine whether the candidate therapeutic agent modulates cholesterol metabolism in the cell.

3. The method of claim 2, wherein the cell is in a mammal.

4. The method of claim 3, wherein the compound is administered to the cell by administration to the mammal.

5. The method of claim 1, wherein the ligand for FXR is a peptide sensor.

6. The method of claim 5, wherein the peptide sensor is derived from a coactivator or corepressor.

7. The method of claim 6, wherein the coactivator is SRC-1.

8. The method of claim 7, wherein the peptide sensor comprises an amino acid sequence LXXLL, wherein L is leucine and X is any amino acid.

9. The method of claim 5, wherein the peptide sensor comprises a detectable label.

10. The method of claim 1, wherein the ligand is a bile acid or bile acid derivative.

11. The method of claim 10, wherein said bile acid is a member selected from the group consisting of CDCA, GCDCA, TCDCA, GCA, TCA, DCA and CA.

12. The method of claim 11, wherein said bile acid is CDCA.

13. The method of claim 1, wherein the ligand is a coactivator or corepressor.

14. The method of claim 13, wherein the coactivator is SRC-1.

15. The method of claim 1, wherein the amount of binding is determined using a FRET assay.

16. The method of claim 1, wherein the amount of binding is determined using a fluorescence polarization assay.

17. The method of claim 1, wherein the amount of binding is determined using ELISA.

18. The method of claim 1, wherein the amount of binding is determined using a direct binding assay.

19. A method for increasing cholesterol metabolism in a cell, said method comprising contacting said cell with a compound that modulates the binding of FXR to a ligand of FXR.

20. The method in accordance with claim 19, wherein said ligand of FXR is a bile acid.

21. The method in accordance with claim 20, wherein said bile acid is a member selected from the group consisting of CDCA, GCDCA, TCDCA, GCA, TCA, DCA and CA.

22. The method in accordance with claim 21, wherein said bile acid is CDCA.

23. The method in accordance with claim 19, wherein said ligand of FXR is RXR.

24. The method in accordance with claim 19, wherein said ligand of FXR is a coactivator.

25. The method in accordance with claim 19, wherein said ligand of FXR is a corepressor.

26. The method in accordance with claim 19, wherein said compound is an antibody that binds to FXR.

27. The method in accordance with claim 19, wherein said cell is a mammalian cell.

28. The method in accordance with claim 19, wherein said cell is in a mammal.

29. The method in accordance with claim 19, wherein said compound modulates binding of a transcription complex that comprises FXR to a response element.

30. The method in accordance with claim 29, wherein the response element is derived from a region upstream of a cyp7 gene.

31. A method for reducing cholesterol levels in a mammal, said method comprising administering to said mammal a compound that modulates the binding of FXR to a ligand of FXR.

32. The method in accordance with claim 31, wherein said mammal is a human.

33. A method of screening to identify a compound that modulates cholesterol metabolism in a cell, said method comprising:

contacting a cell with a test compound, wherein said cell comprises:
a) a polynucleotide that encodes a polypeptide comprising: 1) a DNA binding domain of a receptor which binds to DNA; and 2) a ligand binding domain that is substantially identical to a ligand binding domain of a FXR;
b) a ligand for FXR; and
c) a reporter gene construct which comprises a response element to which said DNA binding domain can bind, wherein said response element is operably linked to a promoter that is operative in the cell and said promoter is operably linked to a reporter gene; and determining whether said reporter gene is expressed at a higher or lower level in the presence of said test compound compared to said reporter gene expression level in the absence of said test compound, wherein a test compound that causes an increase or decrease in reporter gene expression can modulate cholesterol metabolism in a cell.

34. The method in accordance with claim 33, wherein said polypeptide is FXR.

35. The method in accordance with claim 34, wherein said FXR is a human FXR.

36. The method in accordance with claim 34, wherein increased expression of said reporter gene in the presence of said test compound is indicative of increased cholesterol metabolism.

37. The method in accordance with claim 33, wherein said cell also comprises an RXR polypeptide.

38. The method in accordance with claim 37, wherein said RXR polypeptide is a human RXR polypeptide.

39. The method in accordance with claim 33, wherein said FXR is a human FXR.

40. The method in accordance with claim 33, wherein said DNA binding domain is derived from a receptor selected from the group consisting of an estrogen receptor, a progesterone receptor, a glucocorticoid receptor, an androgen receptor, a mineralcorticoid receptor, a vitamin D receptor, a retinoid receptor, and a thyroid hormone receptor.

41. The method in accordance with claim 33, wherein DNA binding domain is a GAL4 DNA binding domain.

42. The method in accordance with claim 41, wherein increased expression of said reporter gene in the presence of said test compound is indicative of increased ability of the compound to stimulate cholesterol metabolism.

43. The method in accordance with claim 33, wherein said DNA binding domain is substantially identical to a DNA binding domain of a FXR.

44. The method in accordance with claim 43, wherein said response element is derived from an upstream region of a cyp7 gene.

45. The method in accordance with claim 44, wherein decreased expression of said reporter gene in the presence of said test compound is indicative of increased ability of the compound to stimulate cholesterol metabolism.

46. The method in accordance with claim 33, wherein said bile acid is a member selected from the grouponsisting of CDCA, GCDCA, TCDCA, GCA, TCA, DCA and CA.

47. The method in accordance with claim 46, wherein said bile acid is CDCA.

* * * * *